United States Patent [19]

Pompon et al.

[11] Patent Number: 5,635,369
[45] Date of Patent: Jun. 3, 1997

[54] YEAST STRAINS WITH STABLE INTEGRATION OF HETEROLOGOUS GENES

[75] Inventors: Denis Pompon, Gif Sur Yvette; Christophe Cullin, Antony; Gilles Truan, Les Ulis; Philippe Urban, Bagneux; Piotr Slonimski, Gif Sur Yvette, all of France

[73] Assignee: Centre National De La Recherche Scientifique, Paris Cedex, France

[21] Appl. No.: 182,127

[22] PCT Filed: Jul. 15, 1992

[86] PCT No.: PCT/FR92/00682

§ 371 Date: Jan. 13, 1994

§ 102(e) Date: Jan. 13, 1994

[87] PCT Pub. No.: WO93/02200

PCT Pub. Date: Feb. 4, 1993

[30] Foreign Application Priority Data

Jul. 15, 1991 [FR] France ..................... 9108884

[51] Int. Cl.[6] ................. C12P 21/02; C12N 1/15
[52] U.S. Cl. ............... 435/69.1; 435/172.3; 435/183; 435/189; 435/254.2; 435/254.21
[58] Field of Search ................... 435/255, 256, 435/183, 189, 69.1, 172.3, 254.2, 254.21

[56] References Cited

U.S. PATENT DOCUMENTS 5,312,735  5/1994  Fink et al. .................... 435/69.1

FOREIGN PATENT DOCUMENTS 0399455  11/1990  European Pat. Off. ........ C12N 15/14

OTHER PUBLICATIONS

Urban et al., *Biochimie*, vol. 72, 1990, pp. 463–472.

Cullin, C. and Pompon, D. "Synthesis of functional mouse cytochromes P–450 P1and chimeric P450 P3–1 in the yeast Saccharomyces cerevisiae," Gene, vol. 65, pp. 203–217 (1988).

*Primary Examiner*—James S. Ketter
*Attorney, Agent, or Firm*—Cooley, Godward, Castro, Huddleson & Tatum

[57] ABSTRACT

Yeast strains and a method of expression in yeast of the monooxygenase activity of heterologous cytochromes P450 are disclosed. Within the genome of the yeast strain, genes for NADPH-cytochrome P450 reductase and cytochrome b5 are stably integrated and coexpressed. The genome is transformed with a plasmid carrying a cassette for the expression of a heterologous P450 gene.

16 Claims, 13 Drawing Sheets

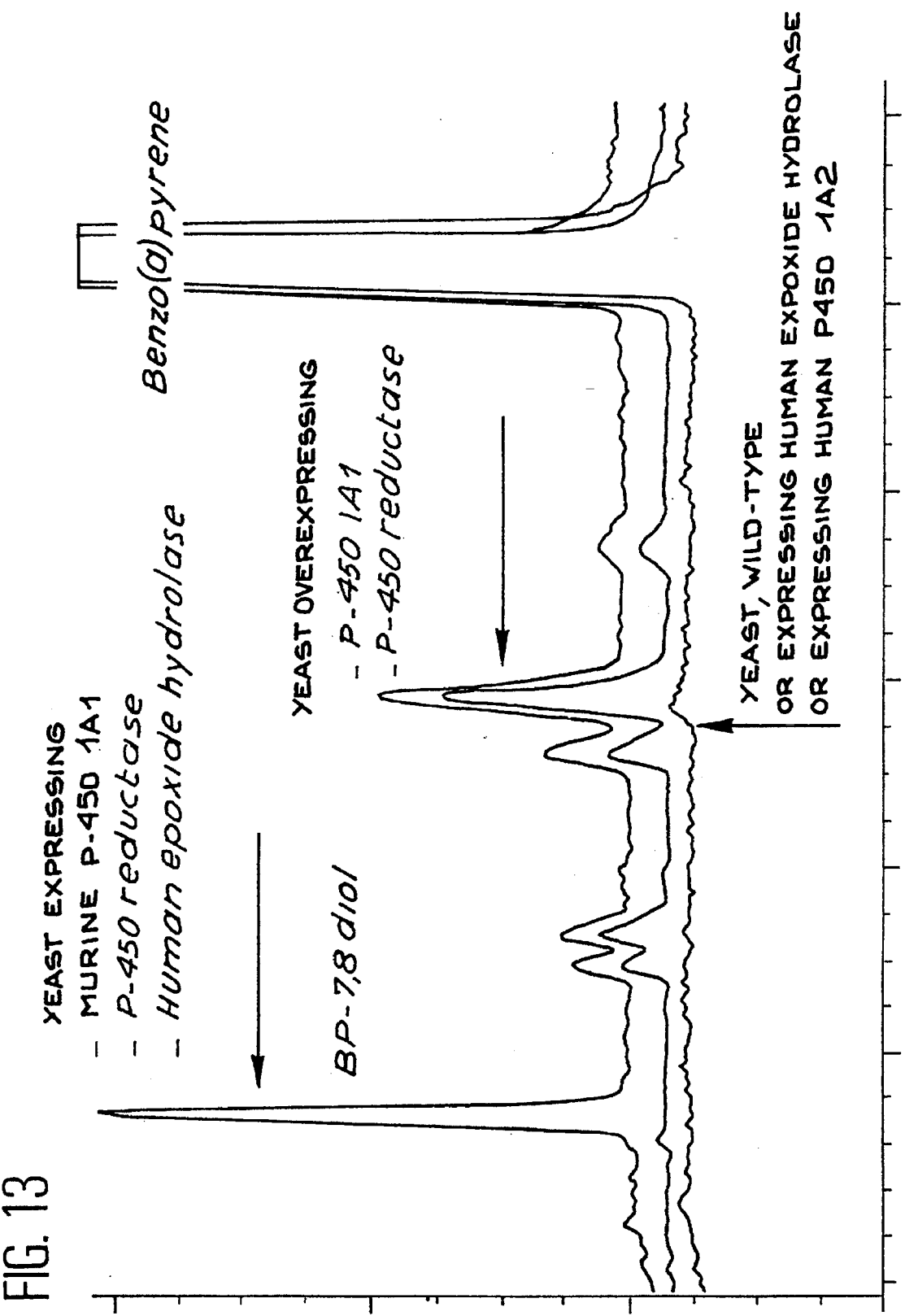

YEAST STRAINS WITH STABLE INTEGRATION OF HETEROLOGOUS GENES

FIELD OF THE INVENTION

The present invention relates to a yeast strain in the chromosomes of which several heterologous genes are stably integrated. The present invention relates, in addition, to a method of expression in yeast of a complex function linked to the activity of several heterologous factors, and especially to a method of expression in yeast of the monooxygenase activity of heterologous cytochrome(s) P450.

BACKGROUND OF THE INVENTION

The cytochromes P450 (hereinafter abbreviated to P450) constitute a superfamily of membrane enzymes having very varied monooxygenase type activities. Their activities are capable of being used in a wide range of fields of application. There may be mentioned, by way of non-limiting examples:

the bioconversion of a virtually unlimited number of lipophilic molecules by means of reactions of insertion of an oxygen atom, followed or otherwise by rearrangements in carbon—carbon or carbon-hydrogen bonds, and by means of the addition of oxygen to a variety of hetero atoms (sulfur, nitrogen, phosphorus). P450 utilizes aerial oxygen as oxidizing agent.

in vitro diagnosis of the formation of toxic or mutagenic metabolites by human hepatic metabolism of natural or artificial xenobiotic molecules (pollutants, medicinal products, additives). Such prediction is of primary importance, especially in the case of the development of new molecules of pharmaceutical importance.

The identification and destruction of molecules which are toxic or pollute the environment.

In view of this broad field of application, the expression of heterologous forms of P450 and of their activities in microorganisms which lack them clearly merits attention. Two problems then became apparent: first, the membrane nature of the P450 of eukaryotes makes it desirable to use a host microorganism of the eukaryotic type, leading to the choice of yeasts; second, these enzymes are functional only in the presence of "associated enzymes" which play the part of specific electron transporters. Whereas the diversity of cytochromes P450 is extreme, the "associated REDOX enzymes" are few in number and comprise cytochrome b5, NADH-cytochrome b5 reductase and, most especially, NADPH-cytochrome P450 reductase. Moreover, certain enzymes, termed phase II, such as, for example, microsomal epoxide hydrolase, may be needed for the metabolic coupling between different P450's, or for the destruction of highly reactive chemical intermediates formed during certain reactions, such as, for example, the metabolism of polycyclic hydrocarbons.

The high level in vivo expression of heterologous cytochromes P450 in yeast leads to high levels of activity only if these "associated redox enzymes", which are essential to the functioning of P450, can be coexpressed in the yeast, in suitable stoichiometries relative to one another and to the P450. Recent data show that, too low a reductase/heterologous P450 mole ratio leads to a low specific activity as a result of the lack of reductase.

too high a reductase/heterologous P450 mole ratio leads to the destruction of a considerable fraction of the P450 as a result of the large increase in the number of abortive catalytic cycles and of the production by the excess of reductase of oxygen-containing radicals which are dangerous to the cell. The outcome is a loss of viability of the cells, or even a drop in activity due to the destruction of cytochromes P450.

too low a cytochrome b5/P450 mole ratio leads to a reduced activity of class B P450. Moreover, the presence of a high level of cytochrome b5 appears to exert a protective effect against the toxic effects linked to excessive reductase levels;

too high a cytochrome b5/P450 mole ratio leads to the inhibition of class A P450 activity, and can potentially reduce the amount of unbound intracellular heme and thus be toxic to the cell.

In order to solve these problems, there was constructed according to the invention, by genomic integration of synthetic genes, a set of yeast strains expressing, stably and in a manner which can be modulated (by the composition of the culture medium), an enzymatic environment which can be optimized for expression of the activity of any heterologous P450.

Many publications have described the expression of heterologous cytochromes P450 in yeast. Nevertheless, the problem of optimization of the cellular environment to permit high activity in vivo has seldom been tackled, the proteins produced often being used for analytical purposes or purposes of in vitro research.

The problem of optimization of the activities has been tackled hitherto in two ways:

by the construction of fusion proteins artificially combining an NADPH-cytochrome P450 reductase (homologous or heterologous) and the cytochrome P450 itself on the same polypeptide chain.

by the use of a vector carrying both an expression unit for the P450 reductase and an expression unit for a heterologous P450 on the same plasmid.

Both of these systems, namely the construction of fusion proteins (P450—P450 reductase) or of plasmid coexpression vectors, possess serious drawbacks:

1—the construction of fusion proteins (P450-reductase) is a lengthy operation which is difficult to optimize (except empirically by a trial-and-error approach), in the present state of knowledge, in respect of the molecular design of the fusion. This is not a priori a genuine defect when attention is focused on a single activity and when lengthy research can be devoted to it; it is, however, a serious weakness during a process of development where several types of activity have to be tested in a reasonable time in order to adjust the tool to the problem. Apart from this fact, this system possesses three major defects which are inherent in it:

the first is that it does not permit an adjustment of the ratio of the amount of reductase to that of the P450. Since the reductase has a priori a much faster catalytic cycle than the cytochrome, the optimum ratio for the activity is not necessarily 1:1, and can vary from one P450 to another, or even from one substrate to another for the same P450.

the second stems from the poor yield of synthesis (or from poor stability) of the fusion protein; this manifests itself in most cases in a large reduction in the level of expression of the fusion protein relative to that of the P450 expressed alone. This decrease causes most, if not all, of the gain in specific activity resulting from the fusion to be lost in terms of yield.

the third defect is the impossibility, if not technical, then at least practical, of generalizing this approach to the fusion of more than two proteins.

2—The coexpression of several heterologous proteins from a single plasmid appears at first sight to be a good approach. Nevertheless, such large plasmids are potentially unstable genetically, most especially (and this is most often the case) when the same promoter elements are used for the different genes. This instability is a definite problem for an industrial application.

Moreover, the multicopy plasmids used, as a result of the random distribution of the number of copies in each cell, lead to cell populations which are very heterogeneous as regards the level of expression of each of these two enzymes (reductase and P450). The mono-oxygenase activity obtained (which is in practice the useful value) is then the mean of a square-law distribution; this value is bound, for obvious reasons, to be lower than the activity value which would be achieved if the P450 (even on a multicopy plasmid) were expressed in a cellular context having a homogeneous and high level of reductase.

SUMMARY OF THE INVENTION

According to the present invention, the method of expression in yeast of the monooxygenase activity of heterologous cytochromes P450 is characterized in that a yeast strain in the genome of which the NADPH-cytochrome P450 reductase and cytochrome b5 genes are integrated, and which hence coexpress the NADPH reductase and cytochrome b5, is transformed with a plasmid carrying a cassette for the expression of the heterologous cytochrome P450 gene.

The stability of the yeast strains which express a context suited to the expression of heterologous P450 is an essential feature in view of the possible generally toxic character, with respect to the cell, of the expression of activity of heterologous P450's and of their associated enzymes. This problem assumes, in effect, critical importance when many foreign genes have to be integrated simultaneously.

The main foreseeable genetic instabilities which lead to the disappearance or modification of heterologous activities introduced into yeast strains carrying one or more foreign genes are:

(a) inactivation by mutation of one of the heterologous genes. Such an event is generally selected spontaneously as a result of the toxicity to the cell of the heterologous genes or at least of the associated activities.

(b) deletion by recombination of the heterologous gene on duplication of the wild-type gene (conversion) within a heterozygous locus (see Diagram 1). The selective advantage is twofold, since it has both an identical effect to (a) and an effect which leads to a wild-type homozygous context.

Diagram 1:
... XXX ... YYYY ... ZZZ→ ... XXX ... YYYY ... ZZZ ...
... XXX ... hhhhh ... ZZZ → ... XXX ... YYYY ... ZZZ ...

XXX and ZZZ : wild-type intergenetic sequences
hhhhhh : heterologous gene
YYYYY : wild-type gene which is the target of the integration (c) elimination of one of the heterologous genes, or evolution of important characteristics of the strain (linked to the rearrangement of unknown endogenous heterozygous genes which are not directly linked to the heterologous genes but have significant functions for the activities of interest) by a meiotic recombination which might occur at the heterozygous loci and which would be followed by sporulations and then by spontaneous crosses.

Consideration of these mechanisms led to a defining of the rules of stability for the construction of multi-integrated strains according to the invention.

In its most general aspect, the subject of the present invention is a yeast strain in the chromosomal genome of which several heterologous genes are stably integrated, and which permits their expression, characterized in that:

1—the yeast strain is a diploid strain in which the alleles are isogenic, with the exception of the loci which carry the heterologous genes and of the mating-type locus, which are heterozygous, 2—the heterozygous loci lack an allele carrying a wild-type gene, and 3—the heterologous genes are placed under the control of an inducible and regulable promoter.

Preferably, each heterozygous locus possesses no sequence homology between the two alleles (the alleles in question hence contain heterologous or artificial genes), or the sequences which are homologous between two alleles in each heterozygote are oriented in opposite directions as regards the reading direction.

Preferably, units for the expression of the heterologous genes, including the elements providing for expression and the structural gene, contain a selectable marker when said heterologous gene constitutes a negative factor for the rate of growth of the strain.

In an especially suitable embodiment, the same genomic locus on each allele is used for the expression of two different heterologous genes, which also form a heterozygous diploid locus.

The heterologous genes are placed under the control of an inducible promoter which is preferably highly regulable, for example by a factor of at least 100, which enables the counterselection responsible for the type (a) instabilities mentioned above to be eliminated.

The use of diploid strains which are completely isogenic, with the exception of the locus which carries the heterologous genes and of the mating-type locus (illustrated below by the construction of the strains PES1-34 and PES1-53) permits a reduction of the type (c) instabilities.

The absence in the diploids of wild-type (or functionally equivalent) copies at the heterozygous loci, it being possible for each heterozygous locus to consist of heterologous genes (or artificial genes, as, for example, the cassette GAL10-CYC1-Yred-tPGK) which satisfy the criterion either of a heterologous gene and or of a deletion (optionally containing a marker), enables the type (b) instabilities mentioned above to be reduced while eliminating the selective advantage of a conversion.

The absence in each heterozygous locus of sequence homology between the two alleles which contain heterologous or artificial genes, or, failing this as in the case of PES1-34 and PES1-53, the use of a reverse orientation of the possible homologous sequences, permits reduction of the types (b) or (c) instabilities mentioned above.

The presence of a selectable marker is appropriate in all units for heterologous expression which do not induce a readily identifiable phenotype, or, at the least, in any allele which carries a heterologous function that constitutes a negative factor for the rate of growth under the normal conditions of use of the strain (the marker is pointless in the case where the effect on growth is positive, such as, for example, for the modified reductase gene).

In a suitable embodiment, the yeast strain according to the invention is characterized in that the integrated heterologous genes code for factors that constitute a multistep bioconversion chain or constitute a complex function.

There may be mentioned in particular a strain in which a yeast or heterologous NADPH-cytochrome P450 reductase gene and a heterologous cytochrome b5 gene are stably integrated.

Preferably, the NADPH-cytochrome P450 reductase gene is integrated in the endogenous NADPH-cytochrome P450 reductase locus.

There may also be mentioned more especially a yeast strain which coexpresses human epoxide hydrolase and NADPH-cytochrome P450 reductase, for which the corresponding genes are integrated in the genome of the yeast strain.

Use will be made more especially, according to the invention, of *Saccharomyces cerevisiae* strains.

The strains according to the invention are more especially useful in a method of expression in yeast of the constituent factors of a complex function, in particular a multistep bioconversion chain 3 the main activity of which is linked to a first given heterologous factor, characterized in that a yeast strain according to the invention is transformed, said strain coexpressing the other contributing heterologous factors to the complex function, and in the chromosomal genome of which the corresponding genes to said other factors are integrated, said strain being transformed with a plasmid carrying a cassette for the expression of said first heterologous gene.

In particular, the subject of the present invention is a method of expression in yeast of the monoxygenase activity of heterologous cytochrome P450, characterized in that a yeast strain according to the invention coexpressing NADPH-cytochrome P450 reductase and cytochrome b5, in the genome of which the NADPH-cytochrome P450 reductase and cytochrome b5 genes are integrated, is transformed using a plasmid carrying a cassette for the expression of the heterologous cytochrome P450 gene.

Preferably, the cytochrome b5 will be of the same heterologous species as the cytochrome P450.

In this method, it will be preferable to use human cytochrome b5 as a specific stabilizer of the heterologous cytochromes P450 under conditions where a high level of reductase is expressed, and as a specific activator of some P450's.

Besides a novel and general method for the stable cointegration of several heterologous genes in the yeast genome, the subject of the present invention is its application to the construction of a set, PES1, of strains (P450 Expression Strains series 1) which are more especially suited to expression of the activity of heterologous cytochromes P450. ThePES1 set comprises six haploid source strains (which may be used alone in the case of the strains PES1-3, PES1-3U and PES1-4) and of three diploid strains (PES1-34, PES1-31, PES1-42) formed by combination of the haploid source strains. Each element of this set may be readily transformed with plasmids carrying expression cassettes for heterologous P450's which are a priori of any kind. The set of strains (PES1-3, PES1-3D, PES1-3U, PES1-4, PES1-34, PES1-31, PES1-42) affords a wide variety of contexts as regards the levels of expression of the redox enzymes associated with the functioning of heterologous P450. This set enables the optimal context for the expression of each specific P450 to be determined and then exploited rapidly. The possibilities of extension of this concept to the coexpression of other activities are presented and illustrated by the construction of a strain (PES1-53) which also expresses human microsomal epoxide hydrolase while overexpressing the reductase. The yeast strains which are constructed according to the methods presented and which coexpress heterologous cytochromes P450, a priori of any origin, and their specific enzymatic environment, find their application in the construction of systems of evaluation and simulation of the metabolism of medicinal products and of other xenobiotic molecules, and in the production of multistep bioconversion systems, of detoxification systems or of pollution-clearing systems.

The strains constructed are genetically stable in the absence of any selection. Their main characteristics are:

the strains of this set are completely isogenic with one another, with the exception of the specifically modified loci, in particular the mating-type locus;

an NADPH-cytochrome P450 reductase and a cytochrome b5 are produced in each cell, at a homogeneous level independent of the level and nature of the heterologous cytochrome P450 possibly expressed;

the total level of reductase and of b5 is adjustable by modification of the composition of the culture medium, independently of the level of heterologous P450 possibly expressed;

the maximum total level of expression of the reductase and of b5 can be at least equal (in molar terms and at maximum induction) to that of the heterologous P450 produced;

the minimum levels of the reductase and of heterologous b5 which can be produced (under non-induction conditions) are at least 10-fold lower than the maximum level of the reductase and of b5 defined above;

the reductase may be overproduced independently of the cytochrome b5;

these strains carry the selectable markers needed for the use of common plasmids, and are, independently of the above properties, "good hosts" for the expression of heterologous cytochromes P450.

The invention also consists of the following set (PES1) of haploid and diploid yeast strains:

The Haploid Elements:

the elements PES1-1 and PES1-2 are not in themselves novel, since they are, respectively, the haploid mating type a and alpha forms of *S. cerevisiae* yeast strain W303.1B.

The element PES1-3 is novel; it is constructed from PES1-2 in the following manner:

1—the genomic sequences of PES1-2 yeast lying between the first Kpn1 site located upstream of the endogenous coding frame of NADPH-cytochrome P450 reductase and the first codon of this same coding frame are removed.

2—the sequences removed are replaced, starting from the Kpn1 (half-site) and in the following order, by: the gene encoding orotidine-5-phosphate decarboxylase (of *S. cerevisiae*), a fragment of the GAL10 gene of *S. cerevisiae*), a fragment of the CYC1 gene of *S. cerevisiae* comprising the transcription initiation sequences of this gene and a few nucleotides of synthetic sequence.

The element PES1-4 is also novel; it is deduced from PES1-3 in the following manner:

1—the genomic sequences lying between the Kpn1 half-site immediately preceding the functional URA3 gene of PES1-3 and the first BspMI site encountered on the 5' side (relative to the orientation of the coding frame of the reductase gene) of this position (formerly in the promoter portion of the wild-type NADPH-cytochrome P450 reductase gene) are removed.

2—the whole of the NADPH-450 reductase coding frame (starting from the BamHI site) together with its flanking portion on the 3' side as far as the first BspMI site encountered on the 3' side (same convention as above) is removed.

3—The portion removed is partially replaced, in the following order and starting from the end where the BspMI site encountered on the 3' side was located and in the following order: the gene encoding orotidine-5-phosphate decarboxylase (of *S. cerevisiae*), a fragment of the GAL10 gene of *S. cerevisiae*, a fragment of the CYC1 gene of *S. cerevisiae* comprising the transcription initiation sequences of this gene followed by a few nucleotides of synthetic sequence, and by the complete coding frame of the human cytochrome b5 gene, followed by a short synthetic sequence, followed by a fragment of the phosphoglycerate kinase gene of yeast and comprising the 3'-flanking sequences of this gene.

4—The mating-type sign of the strain is changed from alpha to a.

The Diploid Elements:

The strain PSE1-34 consists of the diploid of the haploid strains PSE1-3 and PSE1-4.

The strain PSE1-31 consists of the diploid of the haploid strains PSE1-3 and PSE1-1.

The strain PSE1-42 consists of the diploid of the haploid strains PSE1-4 and PSE1-2.

The strain PES1-12 consists of the diploid of the haploid strains PSE1-1 and PSE1-2.

Lastly, the subject of the present invention is hence the set of complying yeast strains which permit the expression of heterologous cytochrome P450, it being possible for each member of this set to be transformed with plasmids carrying a cassette for the expression of heterologous cytochrome P450 according to the method of the invention, the different strains of this set having integrated the NADPH-cytochrome P450 reductase and cytochrome b5 genes in the genome of their chromosomes, the respective levels of expression of these genes being variable between the different strains so that this set enables the optimal strain for the expression of each specific cytochrome P450 to be determined.

Other advantages and characteristics of the present invention will become apparent in the light of the detailed description which follows.

BRIEF DESCRIPTION OF THE DRAWINGS AND TABLES

FIG. 13 shows an HPLC separation of the metabolites of benzo(a)pyrene formed on incubation of this pollutant with the strains PES1-2, PES1-3 and PES1-53, or transformed to express murine cytochrome P450 1A1

Table 1 summarizes the significant genotypes of the strains constructed.

Figure 11:
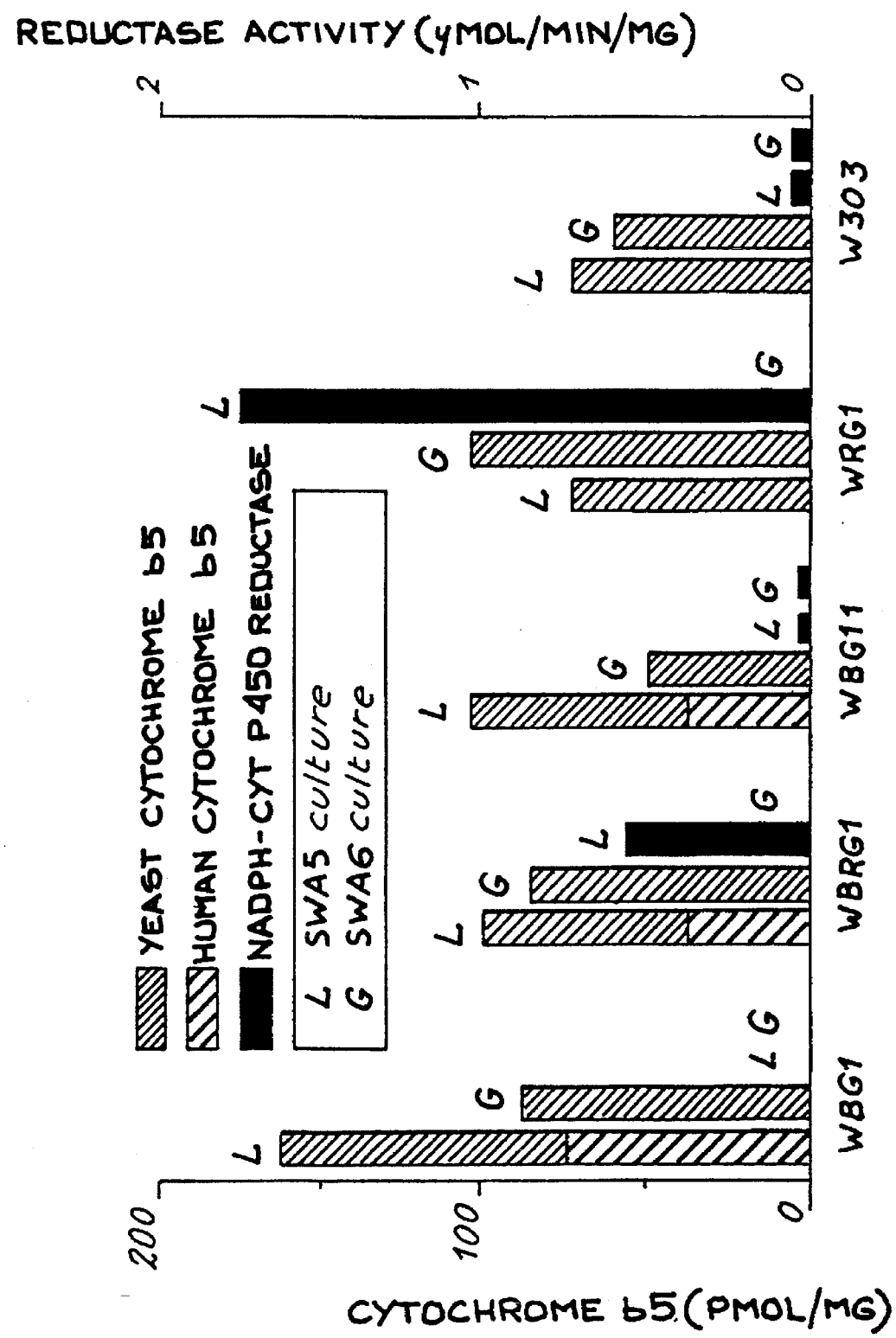
FIG. 11 shows the results of the biochemical assays for the level of expression of NADPH-cytochrome P450 reductase and of cytochrome b5 in the different strains.

Table 2 reproduces the results shown in the diagram of FIG. 11.

Table 3 illustrates the value of the strains constructed for expression of the activity of heterologous cytochrome P450.

DETAILED DESCRIPTION

The method of construction of strains according to the invention falls within the techniques known to a person skilled in the art, and are clarified in the detailed description below, especially the mating-type shift of a haploid by the ho plasmid, followed by crosses of haploids having a different mating-type locus, to obtain diploid strains which are isogenic with the exception of the mating-type locus.

The source yeast strain (W303.1B) is a standard laboratory strain in very widespread use. Its use for expression has been the subject of many publications.

The sequences of all the genes and gene fragments used as source elements in the constructions are published and freely available in the databases. The corresponding DNA fragments were either recloned ab initio in the laboratory by conventional approaches, or recloned by PCR (polymerase chain reaction) from the sequence data in the public domain.

The techniques used for the molecular biology constructions are conventional.

1. Construction of Plasmids 1.1 Genes and DNA Sequences Used human cytochrome b5: the coding frame was recloned by PCR from the published sequence and human liver cDNA (Yoo, M., & Steggles, A. W. (1988) Biochem. Biophys. Res. Commun. 156, 576–580; Urban, P., Cullin, C. & Pompon, D. (1990) Biochimie 72, 463–472).

NADPH-cytochrome P450 reductase: the coding frame of the yeast gene was recloned by PCR from the genomic DNA of the strain PES1-2 and the published sequence (Yabusaki, Y., Murakami, H. & Ohkawa, H. (1988) J. Biochem. (Tokyo) 103, 1004–1010; Urban, 1990). The 5'- and 3'-flanking portions were obtained from a clone isolated in the laboratory in a Hind III genomic fragment library of PES1-2.

Human epoxide hydrolase: the coding frame was cloned by PCR from cDNA, human liver and primers deduced from the published sequence (Skoda, R. C., Demierre, A., McBride, O. W., Gonzalez, F. J., & Meyers, U. A. (1988) J. Biol. Chem. 263, 1549–1554).

URA3 marker and GAL10-CYC1 promoter: the sequences were extracted from plasmid pLGSD5 (Guarente, L., Yocum, R. R. & Gifford, P. (1982) Proc. Natl. Acad. Sci. USA 79, 7410–7414.

PGK gene terminator: the sequences were recloned from the published sequences (Mellow, J., Dobson, M. J., Roberts, N. A., Tulte, M. F., Emtag, J. S., White, S., Lowe, P. A., Patel, T., Kingsman, A. J. & Kingsman, S. M. (1982) Gene 24, 1–14) and PES1-2.

TRP1 marker: the sequence is extracted from plasmid pFL39 (Bonneau, N., Ozier-Kalogeropoulos, O. Li, G., Labouesse, M., Minvielle-Sebastia, L. & Lacroute, F. (1991) Yeast, in press).

1.2. The Plasmid pGP1-PC

Figure 1:
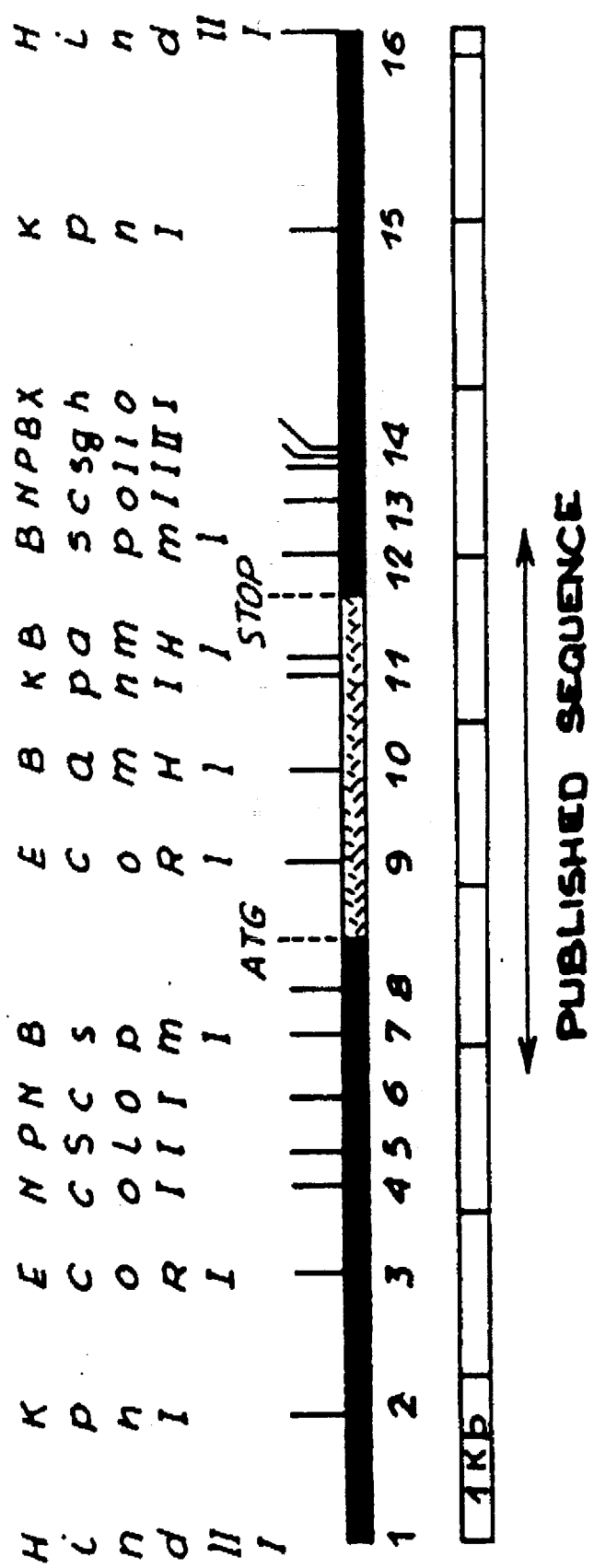
FIG. 1 shows the restriction map of the the genomic DNA of yeast containing the NADPH-cytochrome P450 reductase gene of yeast.
Figure 2:
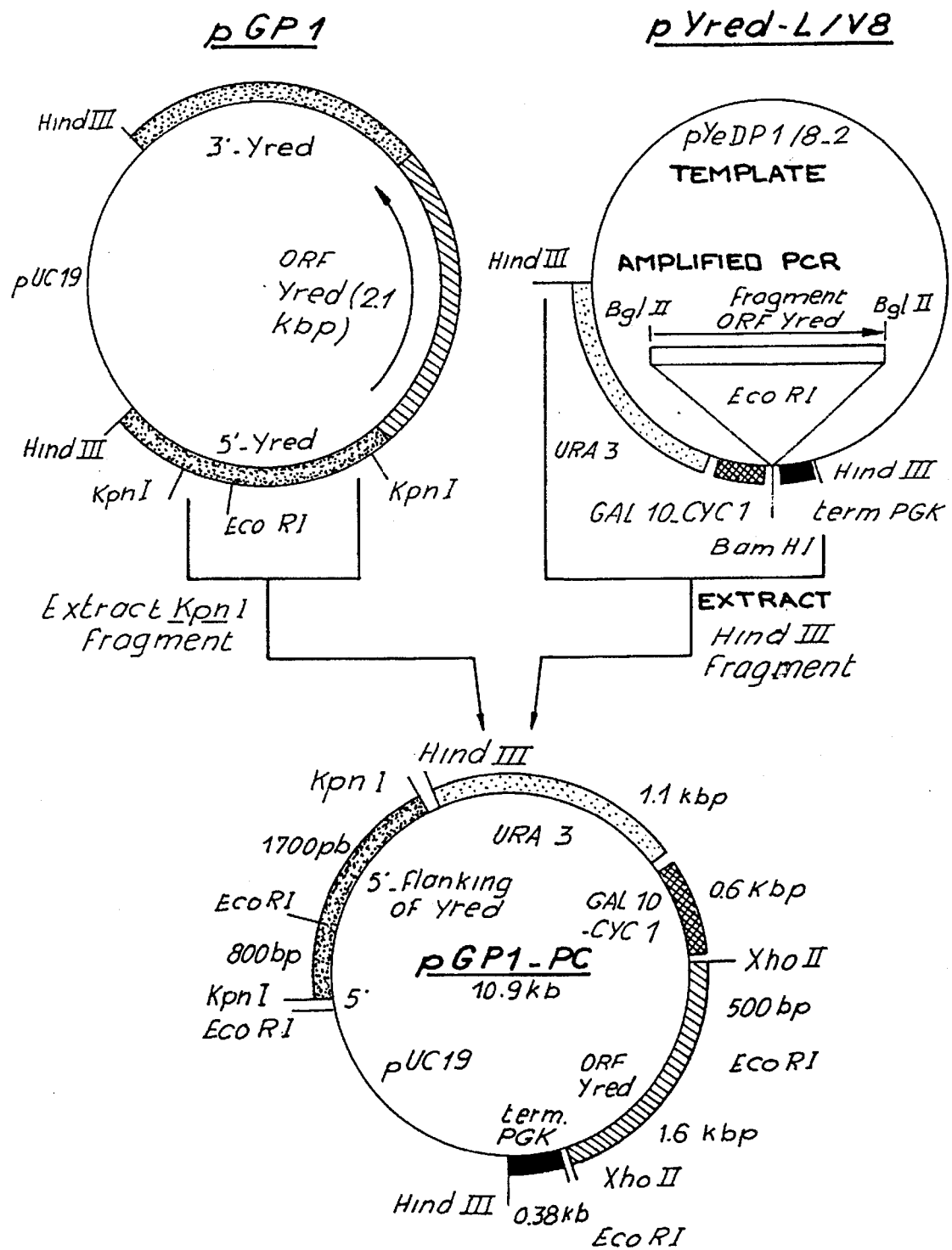
FIG. 2 shows the construction of plasmid PGP1PC from plasmids PGP1 and PYred-L/V8.

The approximately 9-kdp HindIII fragment of yeast genomic DNA, containing the yeast NADPH-cytochrome P450 reductase (Yred) gene, was cloned into pUC19 to give pGP1. The approximate restriction map of the insert is given in attached FIG. 1. The 2.5-kbp Kpn1 fragment, the 3' end of which is located 333 bp on the 5' side of the coding frame of the Yred gene (see FIG. 1), is initially cloned at the Kpn1 site of the vector pUC19 in the orientation which brings the BspMI site, included in the fragment, into proximity with the 5'-non-coding sequences of Yred. The resulting vector pGP1-PC contains approximately 11 kbp (FIG. 2).

1.3 Plasmid pGP1-DT5

Figure 3:
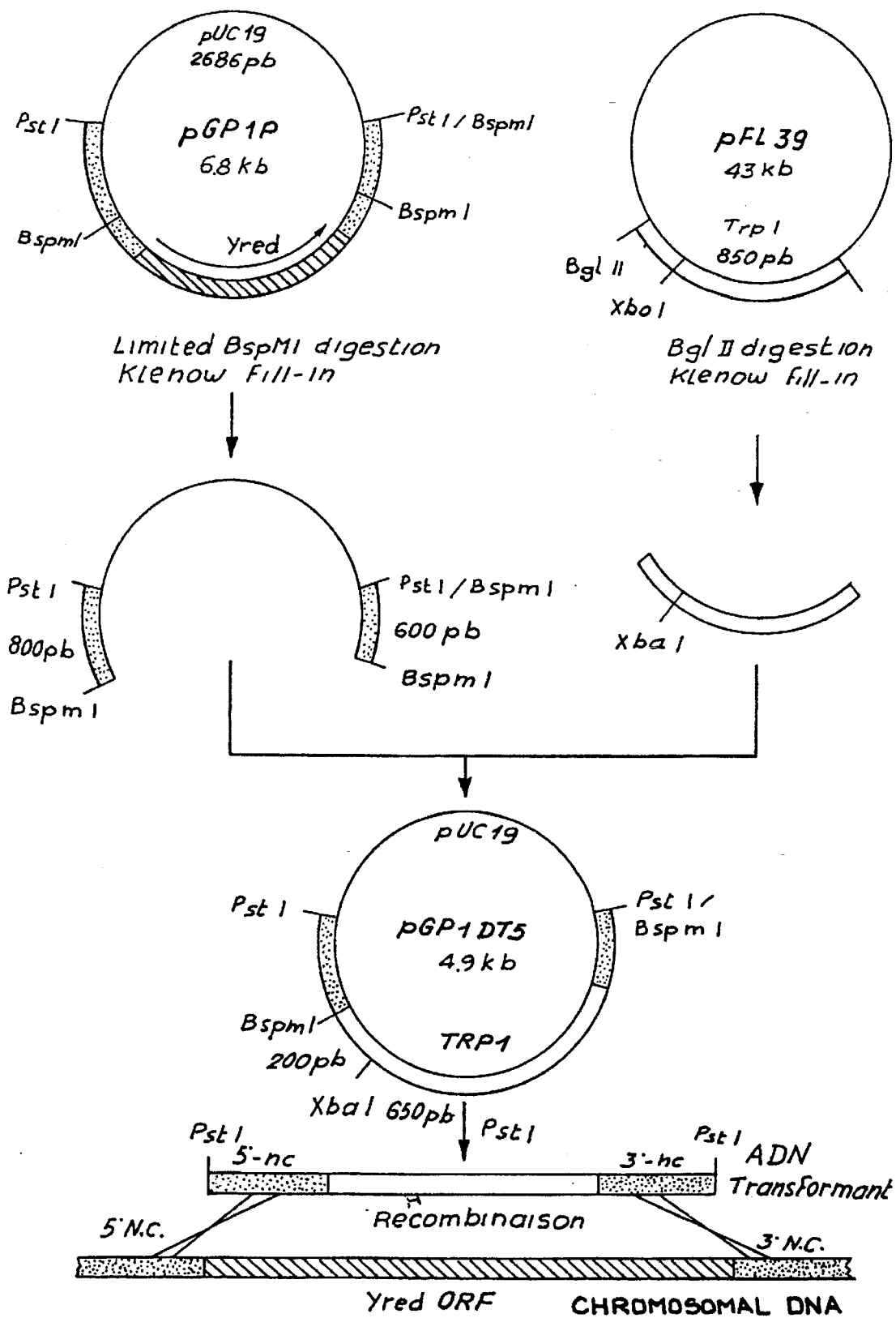
FIG. 3 shows the construction of plasmid PGP1DT5 from plasmids PGP1P and PFL39.

The 4.2-kbp Pst1 fragment of pGP1 which contains the Yred gene is subcloned into the Pst1 site of pUC19 to give pGP1P. Plasmid PGP1P is then subjected to a partial digestion with BspMI, and the 4-kbp fragment resulting therefrom, and which contains pUC19 and the 5'- and 3'-flanking sequences of Yred, is used as a vector for cloning the 850-bp fragment containing the TRP1 gene of yeast (obtained by a total digestion of plasmid pFL39 (Bonneau, 1991) with BglII followed by a treatment with DNA polymerase). The orientation of the cloned fragment is such that the Xba1 site of the TRP1 gene is located 200 bp from the BspMI site of the 5'-flanking portion of the Yred gene (see FIG. 3).

1.4 Plasmid pYeHB1

Figure 4:
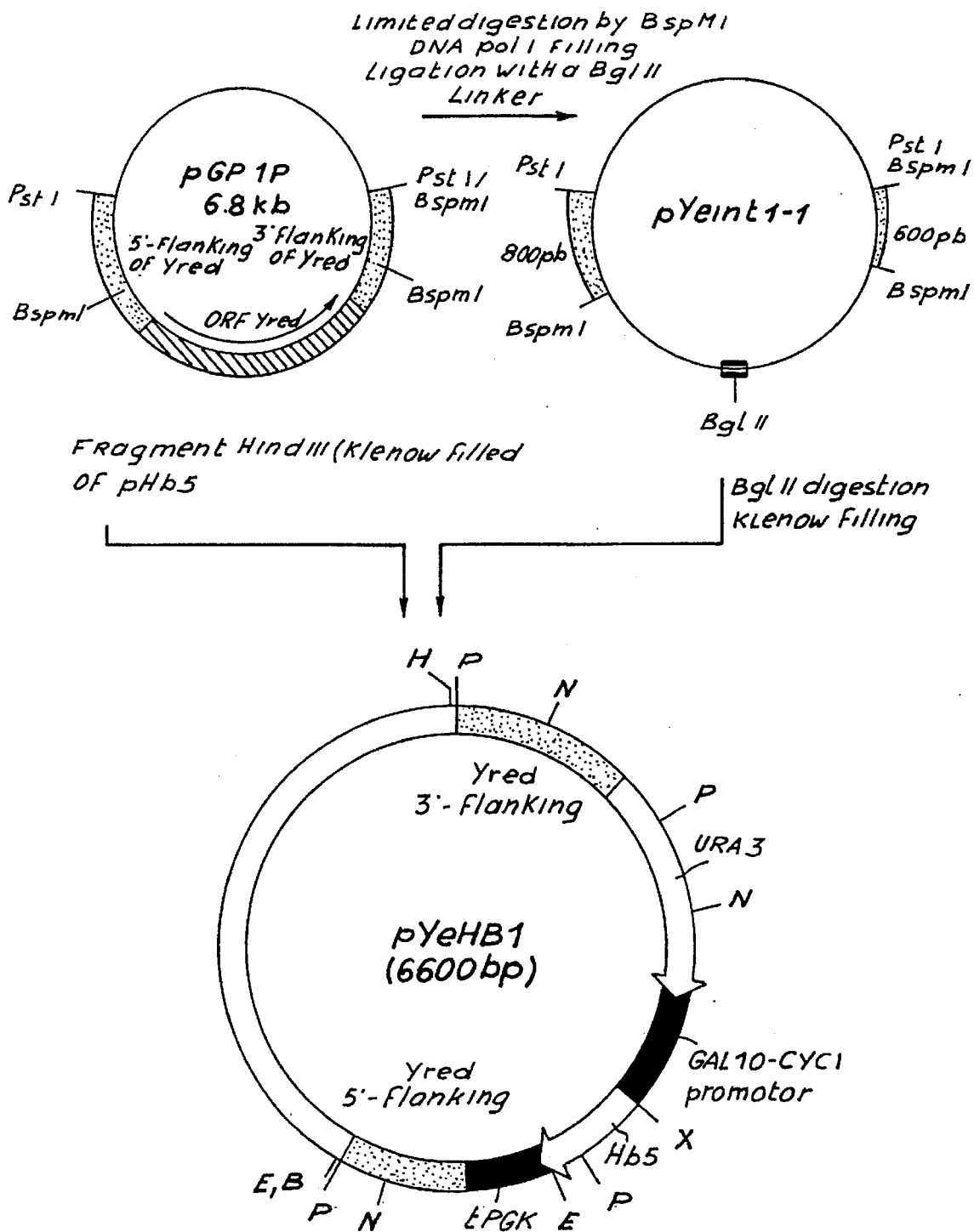
FIG. 4 shows the construction of plasmid PYEHB1 from plasmids PG1P PGP1P PYeINT1-1 and PHb5/V8

Plasmid pGP1P is subjected to a partial digestion with BspMI to remove the 2875-bp fragment carrying the Yred coding frame. This fragment is replaced by a 10-bp oligonucleotide carrying a BglII site, giving pYeint 1-1 (FIG. 4). The 2.5-kbp HindIII fragment of Hb5/V8 (Urban, 1990) which contains the URA3 gene, the GAL10-CYC1 promoter, the human cytochrome b5 coding frame and the terminator portion of the PGK gene is cloned (after being made blunt-ended) into the vector PYeint1-1 opened at the BglII site (site filled in by treatment with DNA pol.1). The selected orientation is such that the resulting vector contains the URA3 gene situated adjacent to the 3'-non-coding portion of the Yred gene (FIG. 4).

1.5 Plasmid pYeHEH

The human microsomal epoxide hydrolase coding frame is amplified by PCR (in a manner similar to the method used to clone cytochrome b5 ) using two complementary primers on 24 nucleotides at the 3' ends of the published sequence. The 5' end of each primer includes a non-homologous BamHI site. The BamHI fragment resulting therefrom is then cloned at the BamHI site of the vector pYeDP ⅛-2 (Cullin, C., & Pompon, D. (1988) Gene 65, 203–217) in the correct orientation. The HindIII fragment which contains the expression cassette is then extracted from the plasmid obtained, and the incoming 3' ends are filled in by a Klenow treatment to permit cloning into the vector PYeINT1-1 opened at the BglII site, then the ends are likewise filled in using Klenow. The selected orientation is such that the vector resulting therefrom contains the URA3 marker situated adjacent to the 3'-non-coding portion of the original Yred gene. Plasmid pYeHEH resulting therefrom is similar to pYeHB1, except for the presence of the human epoxide hydrolass coding frame instead of that of human cytochrome b5.

2. Construction of Yeast Strains 2.1 General

Figure 5:
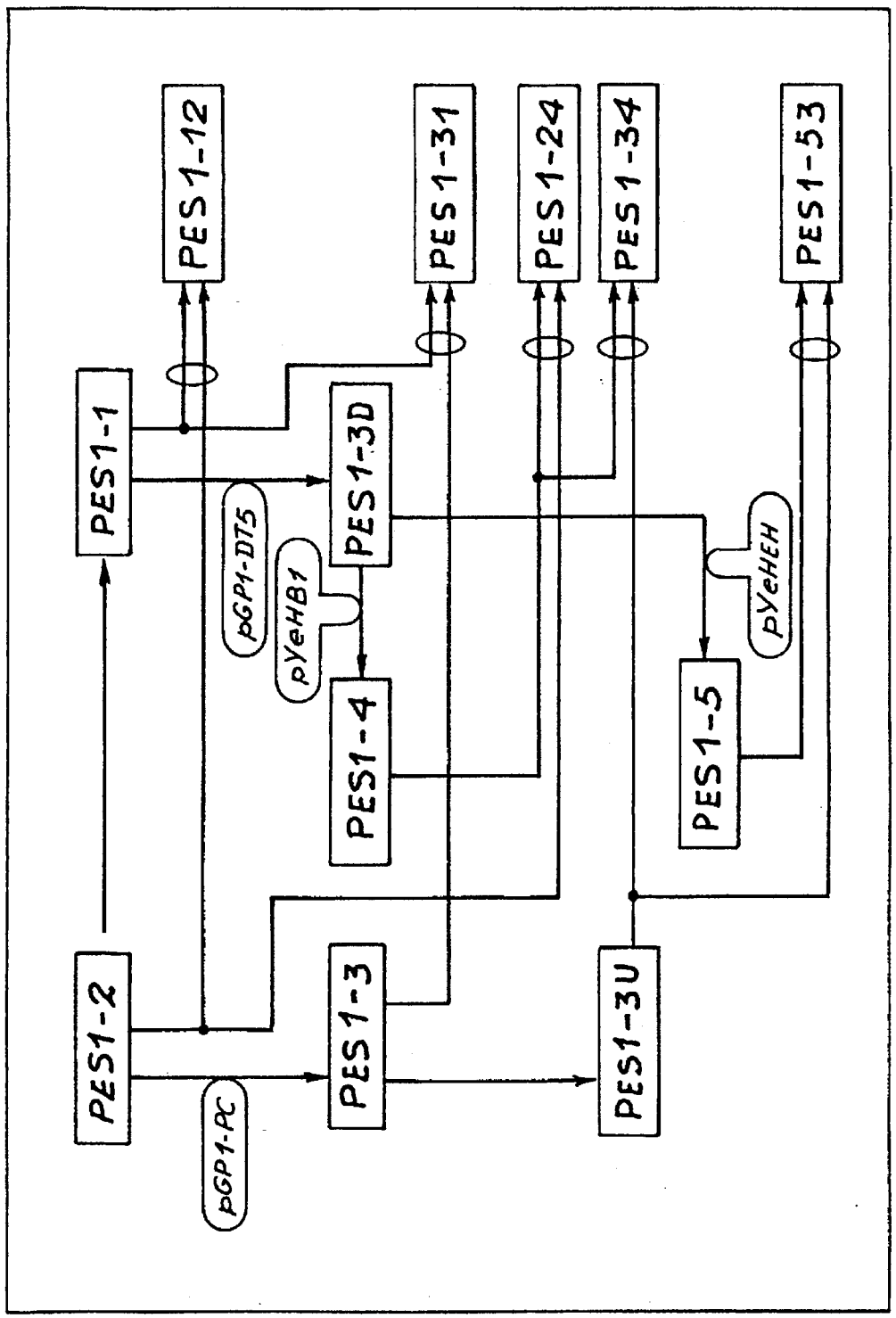
FIG. 5 shows the diagram of construction of the different strains from a single starting strain.
Figure 10:
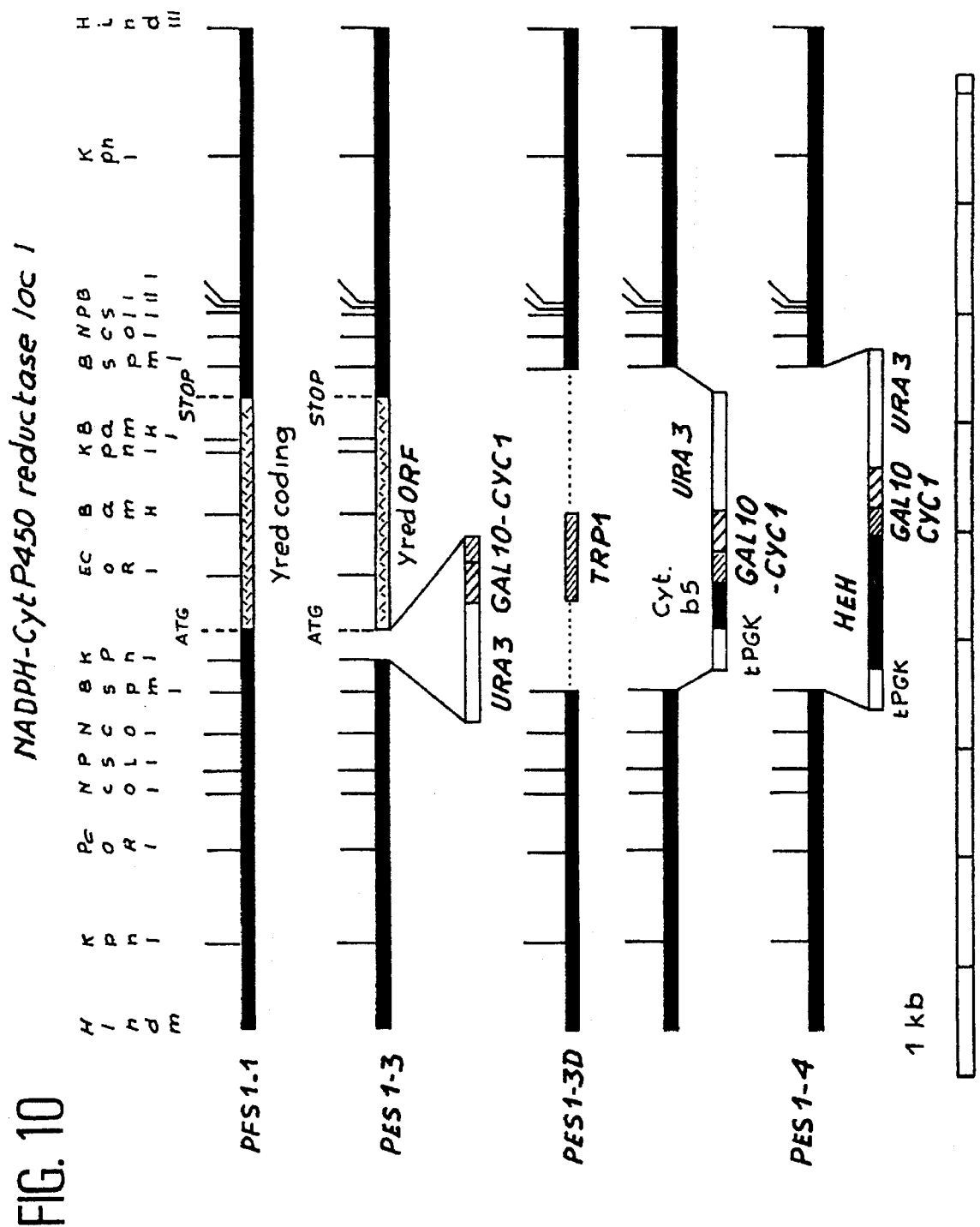
FIG. 10 shows the physical structure of the Yred locus in the different strains.

All the yeast strains were constructed (see FIG. 5) from a single starting strain known to a person skilled in the art under the name W303.1B. This strain is haploid (mating type alpha) and carries as known mutations ura3, Ade2, His 1, Trp1, Leu2; it respires normally and is capable of utilizing galactose as a carbon source. In the interest of homogeneity, this strain is designated hereinafter by the name PES1-2. The structure of the Yred locus of the different strains is summarized diagrammatically in FIG. 10.

2.2 Strain PES1-1

This haploid strain (mating type a) was constructed from the strain PES1-2 by mating-type exchange using the Ho plasmid technique applied according to the published method (Methods in Enzymology, vol. 194, pp 132–146). The strain PES1-1 is hence completely isogenic (with the exception of the mating-type locus) with the strain PES1-2.

2.3 Strain PES1-12

This strain is the diploid resulting simply from the cross between the strains PES1-1 and PES1-2. The diploid character is verified by the faculty of sporulating in an acetate medium. As a result of the construction, this diploid is homozygous for all of its genes (mating-type locus excepted).

2.4 Strain PES1-3 and PES1-3U

Figure 6:
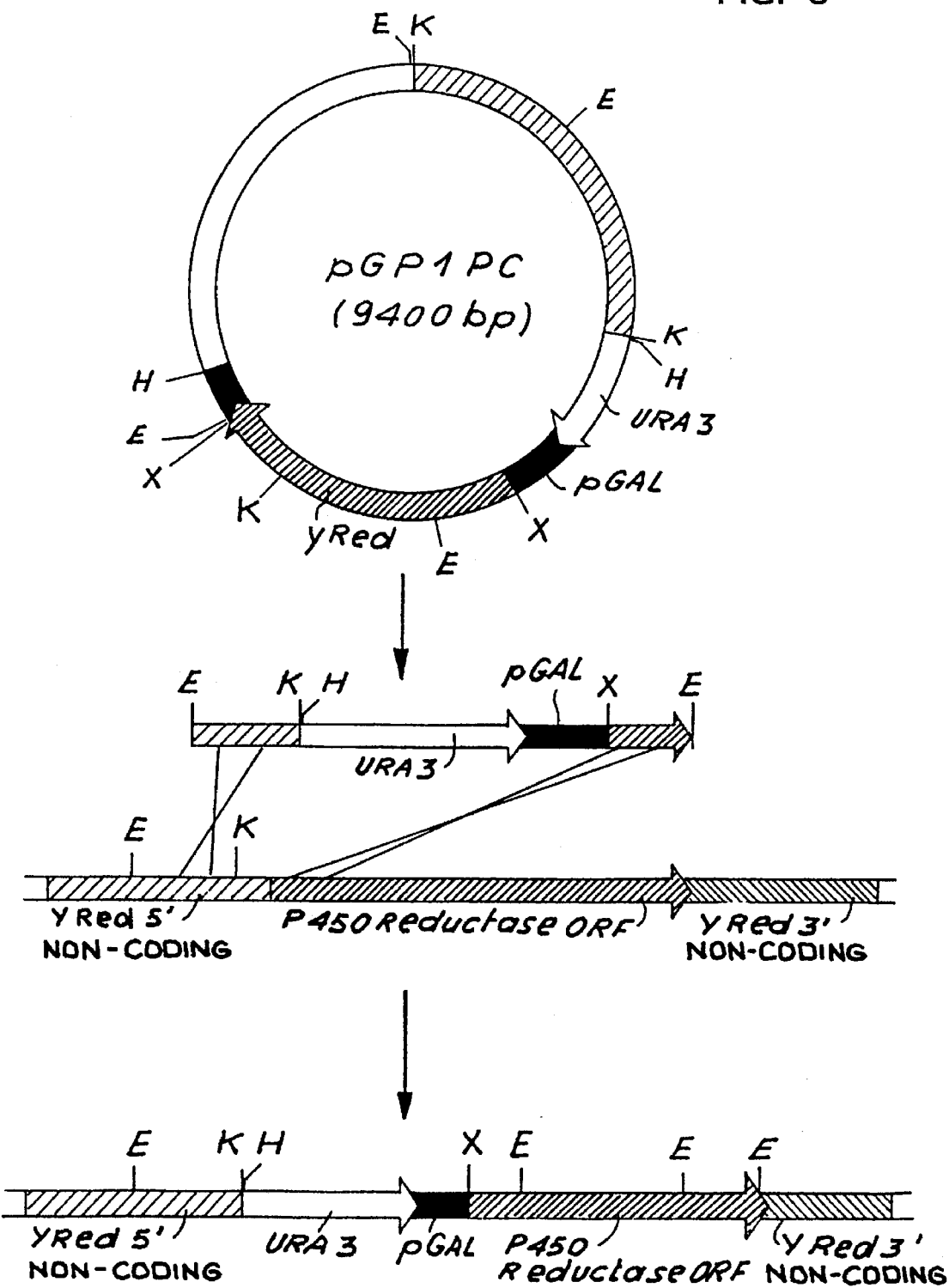
FIG. 6 shows the linearization of plasmid PGP1-PC by an exhaustive digestion using the enzyme Eco RI and the integration by homologous recombination of the resulting fragment in the genome.

This haploid strain (mating type alpha) is completely isogenic with PES1-2, except for the endogenous NADPH-cytochrome P450 reductase locus, which is modified so as to place the natural reductase coding frame under the control of the GAL10-CYC1 inducible promoter by the following procedure:

1—the strain PES1-2 is transformed (using the standard lithium chloride method) with plasmid pGP1-PC doubly linearized by an exhaustive digestion using the enzyme Eco RI (see FIG. 6), and the URA+ transformants are selected.

2—The transformants thus selected are sorted on the basis of a slow growth compared with PES1-2 in glucose-containing complete medium (YPGA) and an identical growth to PES1-2 in galactose-containing complete medium (YPGaIA).

3—one of the clones which satisfies these criteria is chosen and stored under the name PES1-3.

4—spontaneous mutants of ura3 phenotype of PES1-3 are selected by a replica made on a medium containing uracil and 5-fluoroorotic acid. A stable URA⁻mutant (reversion rate less than $10^{-7}$), indistinguishable by any other criterion from PES1-3, is stored under the name PES1-3U.

5—the related genotype at the NADPH-cytochrome P450 reductase locus and phenotype are then tested (see 3.1).

2.5 Strain PES1-3D

Figure 7:
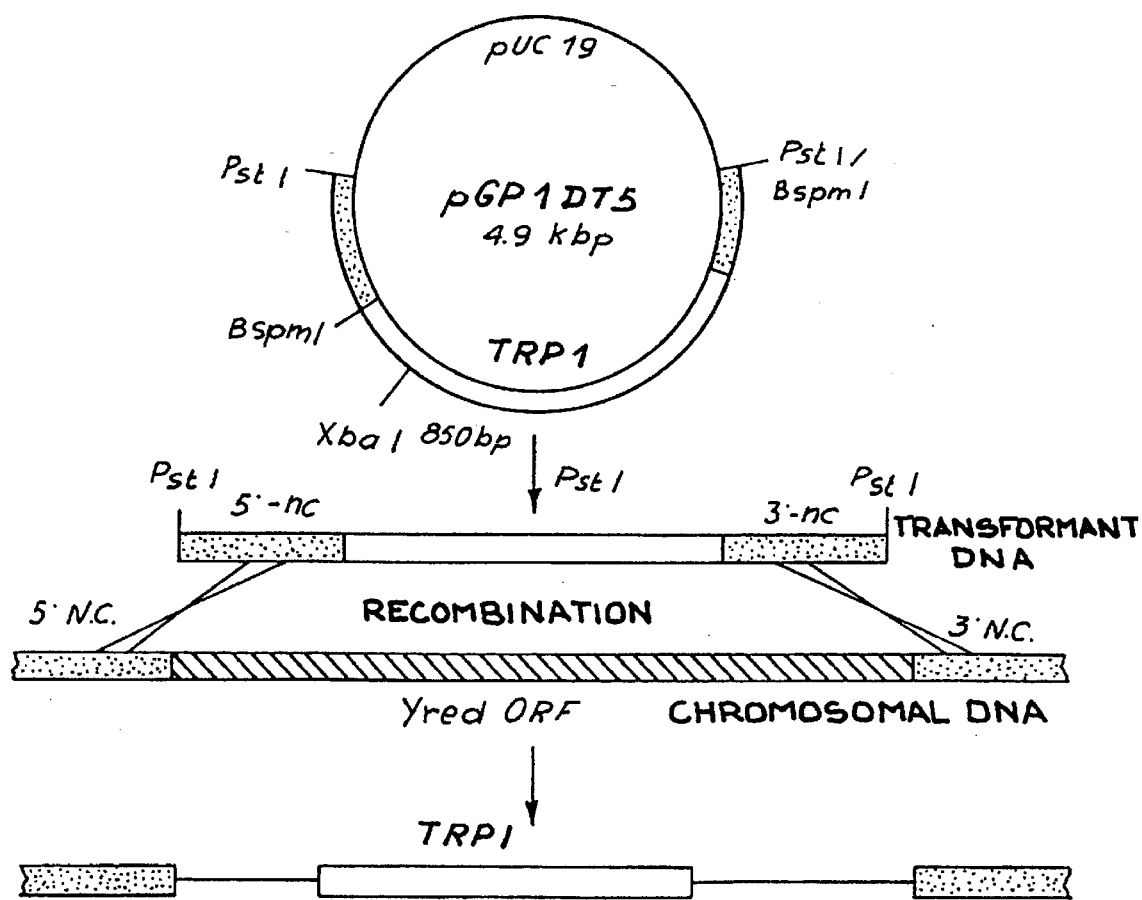
FIG. 7 shows the introduction at the endogenous NADPH-cytochrome P450 reductase locus of the strain PES1-1 of the TRP1 marker to give the strain PES1-3D.

This haploid strain is completely isogenic with PES1-1 except for the endogenous NADPH-cytochrome P450 reductase locus. This locus was modified so as to remove the whole of the coding frame together with a portion of the 5' and 3'-flanking sequences; a TRP1 marker is then introduced at the site of the deletion (see FIG. 7).

1—the diploid strain PES1-12 is transformed (using the standard lithium chloride method) with plasmid pGP1-DT5 doubly linearized by an exhaustive digestion using the enzyme PstI, and the TRP+ transformants are selected.

2—the diploid cells of a few clones thereby obtained are allowed to sporulate on an acetate medium. The resulting tetrads are dissected. The TRP+ haploid clones, which display a slow growth compared to PES1-1 on YPGA glucose-containing complete medium, are selected and then tested by crossing to determine their mating-type sign and their capacity to grow on a galactose-containing medium (YPGalA) and on a glycerol-containing medium (N3).

3—one of the clones of mating-type sign "a" which satisfies these criteria is chosen and stored under the name PES1-3D.

4—the related genotype at the NADPH-cytochrome P450 reductase locus and phenotype are tested (see 3.1).

2.6 Strain PES1-4

Figure 8:
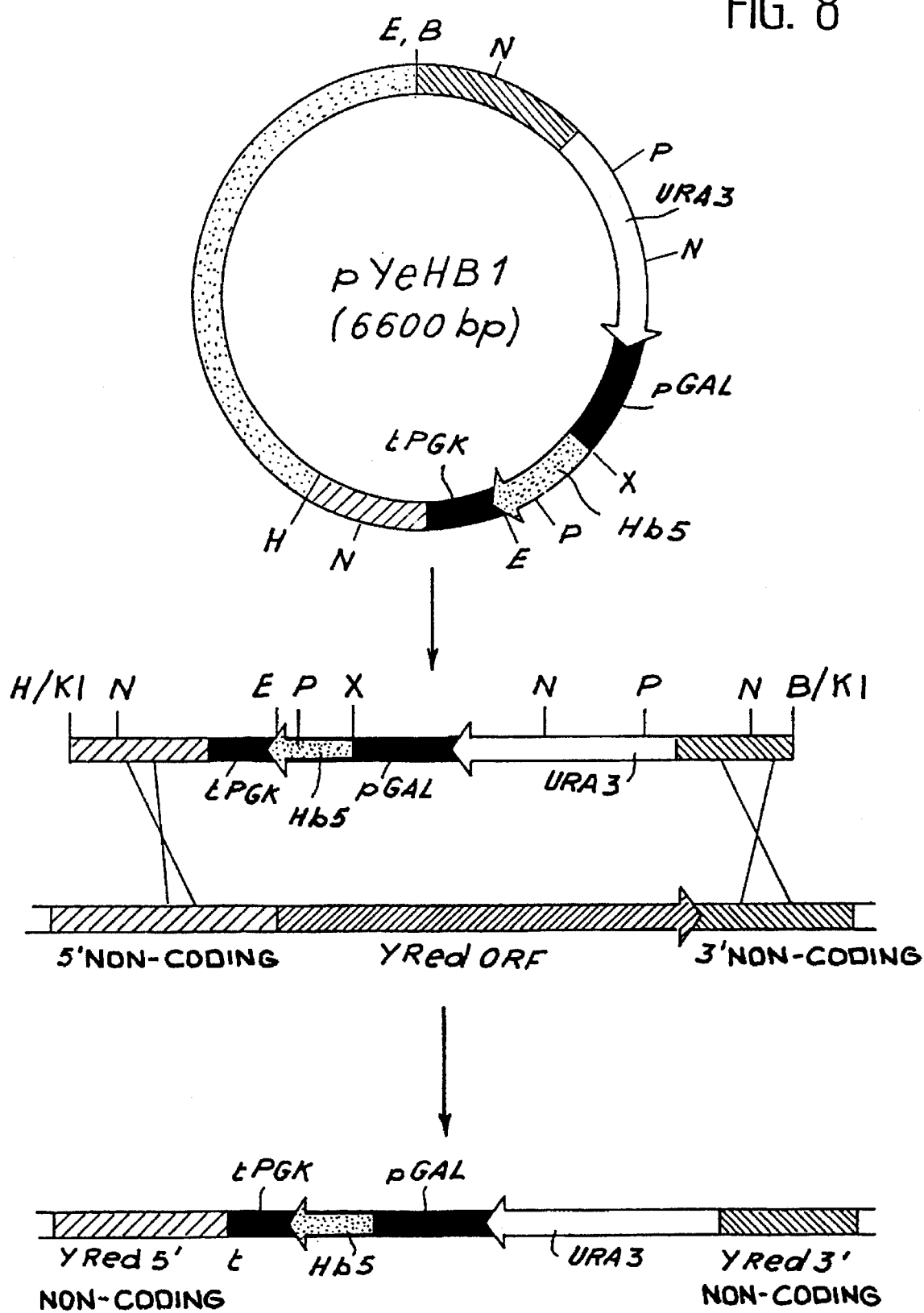
FIG. 8 shows the introduction at the endogenous NADP-cytochrome P450 reductase locus of PES1-1 of an artificial gene consisting of a GAL10-CYC1 hybrid promoter, the human cytochrome b5 coding frame and the terminator portion of the PGK gene, to give the strain PES1-4.

This haploid strain (mating type alpha) is completely isogenic with PES1-1, except for the endogenous NADPH-cytochrome P450 reductase locus. This locus was modified so as to remove the whole of the reductase coding frame (together with a portion of the 5'- and 3'-flanking sequences). An artificial gene consisting of the GAL10-CYC1 hybrid promoter, the human cytochrome b5 coding frame and the terminator portion of the PGK gene is then introduced at the site liberated by the following procedure (see FIG. 8).

The haploid strain PES1-3D is transformed (using the lithium chloride method) with plasmid pYe-HB1 doubly linearized by an exhaustive digestion using the enzymes BamHI and HindIII, and the URA+ transformants are then selected.

The URA+ haploid clones having a TRP⁻ phenotype, a slow growth (compared to PES1-1) on YPGA or YPGalA medium and which grow on glycerol-containing medium (N3) are selected.

The genotype relating to the NADPH-cytochrome P450 reductase locus and the phenotype with respect to cytochrome b5 are tested (see 3.1.).

2.7 Strain PES1-31

This strain is the diploid formed from the strains PES1-3 (URA3) and PES1-1 (Ura3). After growth, the selection is based on testing for URA+ diploids. This strain, like PES1-34 and PES1-42, is heterozygous only for the NADPH-cytochrome P450 reductase locus and for the mating-type locus. One of the copies of the reductase gene is wild-type, the other is under the control of the GAL10-CYC1 promoter (it includes the URA3 marker).

2.8 Strain PES1-34

This strain is the diploid formed from the strains PES1-3U (Ura3) and PES1-4 (URA3). After growth, the selection is based on testing for URA+ diploids. A single modified copy of the reductase gene is present under the control of the GAL10-CYC1 promoter (this strain includes an inactive Ura3 marker), in the other locus the reductase coding frame is deleted and replaced by the expression cassette for cytochrome b5 (which includes a functional URA3 marker).

2.9 Strain PES1-42

This strain is the diploid formed from the strains PES1-4 (URA3) and PES1-2 [lacuna] Ura3). The selection after growth is based on testing for URA+ diploids. This strain contains a single functional wild-type copy of the P450 reductase gene; the second reductase locus is occupied by the expression cassette for cytochrome b5 (which includes a functional URA3 marker).

2.10 Strain PES1-5

Figure 9:
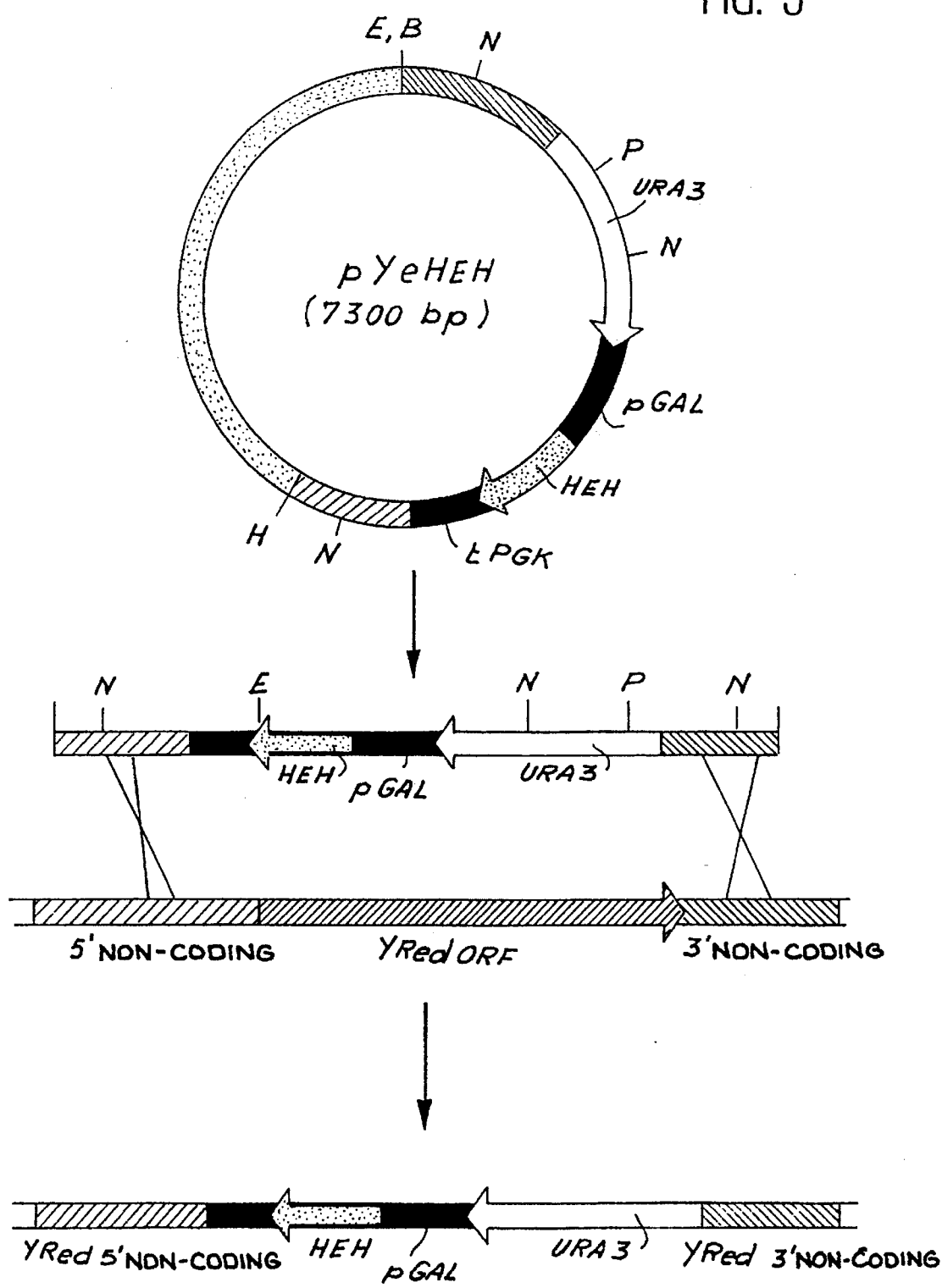
FIG. 9 shows the substitution by an expression cassette for human epoxide hydrolase at the reductase locus of the strain PES1-1 to give the strain PES1-5.

This strain is isogenic with the strain PES1-1 with the exception of the reductase locus, which has been substituted by a cassette for human epoxide hydrolase in the following manner (see FIG. 9):

1—Strain PES1-1 is transformed with the vector pYeHEH linearized by an exhaustive double digestion with the enzymes HindIII and SalI, and the URA3 clones are selected.

2—From the transformants, the clones which have a rate of growth similar to that of PES1-3D on a glucose-containing complete medium (YPGA) and which grow on a glycerol-containing medium (N3) are selected.

3—A clone expressing human epoxide hydrolase is selected and stored under the name PES1-5.

4—The genotype relating to the NADPH-cytochrome P450 reductase locus and the related phenotype with respect to epoxide hydrolase are tested (see 3.1).

2.11 Strain PES1-53

This strain is the diploid formed from the strains PES1-5 and PES1-3U. The selection after growth is based on testing for a URA+ diploid. This diploid strain contains:

on one of the two original reductase loci, the Yred coding frame under the GAL10-CYC1 promoter (this locus contains an inactive Ura3 marker).

the other original reductase locus is deleted and replaced by an expression cassette for human epoxide hydrolase; it also contains an active URA3 marker.

3. Genetic Characterization of the Strains Constructed 3.1 Nature of the Genotypes The significant genotypes of the strains constructed are summarized in Table 1. The physical structure of the Yred locus in the different strains is given in FIG. 10; it was checked as follows:

PES1-1, PES1-2, PES1-12 : wild-type Yred loci.

PES1-3 and PES1-3U: (a1) PCR amplification of the Yred ORF (2.1 kbp) using two primers located, respectively, at the 5' and 3' ends of the coding and non-coding strands of the coding frame. (b1) PCR amplification of a 2.2-kbp band using a first primer located at the 3' end of the GAL10-CYC1 promoter and a second located at the 5' end of the non-coding strand of the coding frame. (c1) Southern blotting of the genomic DNA after a digestion with EcoRI, and visualization with a probe manufactured from the Yred ORF.

PES1-3D: (a2) absence of amplification of the 2.1-kbp and 2.2-kbp bands of the tests "a1 and b1". (b2) Test identical to "c1" using a TRP1 probe.

PES2-4 : (a3) PCR amplification of the cytochrome b5 ORF (405 bp) using two primers located, respectively, at the 5' and 3' ends of the coding and non-coding strands of the coding frame. Absence of amplification as in the test "a2". (b3) PCR amplification of a 0.40-kbp band using a first primer located at the 3' end of the GAL10-CYC1 promoter and a second located at the 5' end of the non-coding strand of the b5 coding frame. (c3) Southern blotting of the genomic DNA after a digestion with EcoRI, followed by visualization with a probe manufactured from the human b5 coding frame.

PES1-31: (a4) tests "b1 and c1", check of the diploid state by sporulation.

PES1-34: (a5) tests "a1,b1,b3,c1,c3", check of the diploid state by sporulation.

PES1-42: (a6) tests "a1,b3,c3", check of the diploid state by sporulation.

PES1-5 and PES1-53: same checks as for PES1-4 and PES1-34, respectively, but using the epoxide hydrolase sequence instead of that of cytochrome b5.

The auxotrophic characters of the set of strains are determined by a replica on dishes of partially supplemented minimum medium.

4. Enzyme Assays 4.1 Cultures and Preparation of Microsomal Fractions

The different strains are cultured at 28° C. with moderate stirring (orbital stirrer at 100 rpm) in a semisynthetic medium composed as follows.

SWA6 medium: D-glucose 20 g/l (w/v), yeast nitrogen base (Difco) 0.7%, (w/v), Casein acid hydrolysate 0.1% (w/v), adenine 40 mg/l, tryptophan 20 mg/l.

SWA5 medium: D-galactose 20 g/l (w/v), yeast nitrogen base (Difco) 0.7% (w/v), Casein acid hydrolysate 0.1% (w/v), adenine 40 mg/l, tryptophan 20 mg/l.

SW6 medium: D-galactose 20 g/l (w/v), yeast nitrogen base (Difco) 0.7% (w/v), Casein acid hydrolysate 0.1% (w/v), tryptophan 20 mg/l.

SW5 medium: D-galactose 20 g/l (w/v), yeast nitrogen base (Difco) 0.7% (v/w [sic]), Casein acid hydrolysate 0.1% (w/v), tryptophan 20 mg/l.

The cultures (250 ml) are arrested when the cell density reaches $2.5 \times 10^7$ cells per ml. The cells are then collected by centrifugation for 5 min at 2500 g. The cell pellet is taken up in 35 ml of 50 mM Tris-HCl buffer pH 7.4, 5 mM EDTA, 100 mM KCl, 20 mM betamercaptoethanol, and the cells are then incubated for 10 min at 20° C. and then recentrifuged for 3 min 10,000 g. The cell pellet is washed with 35 ml of 50 mM Tris-HCl buffer pH 7.4, 1 mM EDTA, 0.6M sorbitol (referred to as rupture buffer), and the cell suspension is then centrifuged in 45-ml screw-capped tubes (as above). A volume of rupture buffer equal to twice the volume of the pellet is then added to form a very dense suspension. Glass beads (of the Braun type 0.45–0.5 mm in diameter) are immediately added in an amount just sufficient to show through the surface of the cell suspension. The tubes are then vigorously shaken (3 shakes per second) vertically for 2 minutes. 3 ml of rupture buffer are then added and the tubes are vortexed for 5 seconds. The liquid present between the beads (but not the beads) is transferred to another tube. 3 ml of rupture buffer are added again to the residual beads, and the operation (vortexing and transfer) is started again. The extraction is repeated a third time. The combined extracts (approximately 10 ml) are centrifuged for 15 min at 10,000 g. The supernatant is transferred to another tube and the volume adjusted to 10 ml with rupture buffer. Three hundred microliters of 4M NaCl solution are added, followed by three and a half milliliters of a 40% (w/v) aqueous solution of polyethylene glycol 4000. The mixture is left for 15 min at 0° C. and then centrifuged for 10 min at 10,000 g. The supernatant is carefully removed, and the surface of the pellet (which contains the microsomal fraction) and of the tube are washed without resuspending the pellet with a small volume of 50 mM Tris-HCl buffer pH 7.4, 1 mM EDTA, 20% (v/v) glycerol (referred to as take-up buffer). The pellet is resuspended in one milliliter of take-up buffer, and the suspension is homogenized by drawing it into and expelling it from a syringe equipped with a needle (bent twice into a Z-shape) 0.3 mm in diameter. The microsomes are then distributed in 200 µl aliquots and stored frozen at −80° C.

4.2 Assay of Activities

NADPH-cytochrome P450 reductase: the activity is tested by measuring the reduction of horse heart cytochrome c (Sigma type VI) at a concentration of 10 µM in the presence of NADPH (100 µg/ml) and in a 50 mM Tris-HCl buffer pH 7.4, 1 mM EDTA. The activity is calculated using a differential coefficient of absorption of 21 mM-1 at 550 nm. One unit of activity is defined as the amount of enzyme (in the form of suspension of microsomes) capable of reducing 1 nanomole of cytochrome c per minute at 20° C. The activity is referred to the total amount of microsomal proteins, determined using Pierce's BCA test.

Cytochrome b5 and cytochrome P450: The concentration of these cytochromes is determined by differential spectrophotometry as described previously (Urban, 1990).

The EROD (ethoxyresorufin O-deethylase) activity of cytochrome P450 1A1 is determined by measuring at 22° C. the increase in fluorescence at 586 nm (excitation adjusted to 530 nm) in a cell containing 50 mM Tris-HCl buffer pH 7.4 1 mM EDTA, 0.1 mg/ml of NADPH, 1 µM 7-ethoxyresorufin and an aliquot (generally: 10 µl of a suspension of microsomes). The activity is calculated and expressed as picomoles of resorufin formed per min after calibration of the apparatus with authentic resorufin.

The testosterone 6beta-hydroxylase activity of P450 IIIA4 is measured by incubating for 15 min an aliquot of the suspension of microsomes (generally: 20 µl) with 230 µl of 50 mM Tris-HCl buffer pH 7.4, 1 mM EDTA, 0.05 mg/ml of NADPH, 80 µM testosterone. The reaction is stopped by adding 5 µl of trifluoroacetic acid, and the aqueous phase is extracted with 500 µl of dichloromethane. After evaporation of the solvent under a stream of nitrogen, the dry residue (steroids) is taken up in 40 µl of a methanol/water (1:3 v/v) mixture, and the metabolites formed are separated by HPLC (high pressure liquid chromatography) on a C18 reversed-phase column eluted with an acetonitrile/water gradient. The identification and quantification of the metabolites are performed by a comparison of calibration with the authentic products.

Epoxide Hydrolase: epoxide hydrolase activity is measured by incubating an aliquot of the suspension of microsomes (generally 40 µl) in 400 µl of 50 mM Tris-HCl buffer pH 7.4, 1 mM EDTA containing 1 mM styrene oxide. The formation of the corresponding diol is quantified by HPLC separation on a C18 reverse column, using the authentic diol as reference.

The Activity of Bioconversion of Benzo(a)pyrene to benzo(a)pyrene-7,8-diol is demonstrated on microsomal fractions of the strain PES1-53 transformed with the expression plasmid ccP1/V60 (Cullin and Pompon, 1990), which codes for the cytochrome P450 of the murine 1A1 family. An amount of yeast microsomes corresponding to 100 µg of total proteins is incubated for 15 minutes with 250 µl of 50 mM Tris-HCl buffer pH 7.4, 1 mM EDTA, 15 µM benzo(a)pyrene and containing 0.1 mg/ml of NADPH. The reaction is stopped by adding 10 µl of trifluoroacetic acid. After saturation of the aqueous phase with sodium chloride and extraction of the metabolites with dichloromethane, the metabolites are separated by C18 reversed-phase HPLC according to standard procedures.

The set of strains constructed constitutes:
  an analytical tool making it possible to identify rapidly the redox enzymatic context associated with P450 which is optimal for the expression of a defined activity of a given P450.
  a production tool, after identification, in this set, of the strain best suited to the requirements.

4.3 The Individual Properties of the Strains of This Set are:

Strain PES1-3:

The genetic engineering work performed on this strain results in destruction of the natural regulation of the yeast NADPH-cytochrome P450 reductase gene, and in placing the synthesis of this protein under the transcriptional control of an artificial hybrid promoter composed of the UAS (upstream activating sequence) of the GAL10 yeast gene and of the transcription initiation sequences of the CYC1 yeast gene.

When cultured on a medium containing galactose, this strain expresses a level of NADPH-cytochrome P450 reductase which is 20 to 30 times as high as the level present in the PES1-2 parent strain.

Conversely, in the absence of galactose, the reductase level present is extremely low (in fact undetectable), that is to say at least 100-fold lower than the level present in the PES1-2 parent.

Expression levels intermediate between these two extremes are possible using either limited times of induction with galactose (0 to 12 hours), or cultures in the presence of a suitable mixture of glucose and galactose.

A very important fact for biotechnological applications should be noted: the strains PSE1-3 and PES1-31 do not contain a DNA sequence exogenous to yeast (especially a bacterial sequence). The rare fragments of synthetic sequence introduced are very short (less than 10 bp), and of "commonplace" sequences likely to be found naturally in many copies in the host.

Strain PES1-4

This strain possesses two characteristics:
it does not express NADPH-cytochrome P450 reductase (neither endogenous nor exogenous).
it expresses both a normal level (that of a wild-type strain) of yeast cytochrome b5 and a conditional level (high in galactose containing culture medium, very low in glucose-containing culture medium) of human cytochrome b5. Consequently, the total level (yeast + human) of cytochrome b5 expressed in the presence of galactose as the sole carbon source is 2 to 3 times as high as the level of endogenous b5 of the haploid wild-type strain PES1-1.

Strain PES1-34

When cultured on a culture medium containing glucose as a carbon source, this strain expresses a total level of NADPH-cytochrome P450 reductase 2-fold lower than the strain PES1-12 (the reference wild-type diploid), a normal level of yeast cytochrome b5 (level of the reference wild-type strain) and a negligible level of human cytochrome b5 (at least 100-fold lower than the level of yeast cytochrome b5).

When cultured on a culture medium containing galactose as a carbon source this strain expresses a total level of NADPH-cytochrome P450 reductase approximately 10 times as high as the level of the reference wild-type strain, a level of yeast cytochrome b5 equivalent to the wild-type level and a level of human cytochrome b5 2 to 3 times as high as the level of yeast cytochrome b5.

Strain PES1-31:

In glucose-containing culture medium, this strain expresses a level of cytochrome P450 reductase equal to one half of the level of the wild-type diploid PES1-21. In galactose-containing culture medium, it expresses a level of NADPH-cytochrome P450 reductase similar to that of the strain PES1-34. This strain does not express heterologous cytochrome b5, but expresses a wild-type level of endogenous cytochrome b5.

Strain PES1-42

Irrespective of the culture conditions (glucose or galactose), this strain expresses the same levels of cytochromes b5 (endogenous and human) as the strain PES1-34, and a reductase level approximately one half that of the wild-type diploid strain PES1-12.

Table 2 summarizes the main characteristics of these strains.

4.4 Results of the Biochemical Assays 4.4.1 Level of Expression of NADPH-cytochrome P450 Reductase and of Cytochrome b5

The level of expression of NADPH-cytochrome P450 [lacuna] and of cytochromes b5 (the endogenous yeast form and the human form) were determined under standard culture conditions (see 4.1) for the strains constructed. The results are presented, on the one hand in Table 2, and on the other hand in diagrammatic form in FIG. 11.

The results call for the following comments:
the reductase activity in the strain PES1-3 cultured in SWA5 galactose-containing medium is increased approximately 30-fold relative to the activity of the wild-type strain. This increase is of the order of 10-fold in the strains PES1-34 and PES1-31. In SWA6 glucose-containing medium (repression medium), the reductase level is, in contrast, undetectable (at least 100-fold lower than the level of the wild-type strain).

the activity of the level of expression of cytochrome b5 gives rise to an analytical problem. In effect, yeast expresses endogenously a cytochrome b5 which is not distinguishable from human cytochrome b5 in the assay test used (which is unrelated to the activity sought but is the only quantitative test available). Endogenous cytochrome b5, though present in substantial amounts, does not appear to be equivalent to mammalian cytochrome b5 for the desired objective, which is the study of the interaction of cytochrome b5 with human P450 produced in yeast, thereby justifying the expression of human heterologous cytochrome b5. The respective contributions of the two forms of cytochrome b5 in the assay used (which assays the sum of the two) may nevertheless be estimated by an analysis of the collective data (see Table 2 and FIG. 11), assuming an expression proportional to the gene assay in the diploid strains. This analysis does not permit an unequivocal calculation of the human cytochrome b5 concentration on account of our lack of knowledge of the mechanisms of regulation of endogenous cytochrome b5 in response to the expression of an exogenous cytochrome b5, but it leads to a range of expression levels centered on an order of magnitude around 100 pmol per mg of microsomal proteins. The important point is that such a level is in correct stoichiometry (P450 forms a 1:1 complex, in molar terms, with b5 ) with the level at which P450 is produced in yeast using current technologies. The small apparent increase (approximately twofold) in the total cytochrome b5 level in the strains constructed is nevertheless functionally very significant on account of the non-equivalence of yeast and human cytochromes b5 (see below).

4.4.2 Influence of the Level of Reductase and of Cytochrome b5 on the Activity of Heterologous Cytochromes P450.

The value of the strains constructed for expression of the activity of heterologous cytochromes P450 is illustrated by examples described in Table 3. These examples are given by way of illustration and are not limitative of possible applications. The data derive from the following experiment:
expression plasmids containing the coding frames of murine cytochrome P450 1A1 and human cytochromes P450 1A1 and 3A4 (subtype NF25) cloned between the BamHI and EcoRI sites of the yeast expression vector pYeDP60 (Cullin, 1988; Renaud, J. P., Cullin, C., Pompon, D., Beaune, P., & Mansuy, D. (1990) Eur. J. Biochem. 194, 889–896; Urban, 1990, Gautier, J. C. et al. (1991), manuscript in preparation) are introduced into the PES1 series strains (by lithium chloride transformation), and the clones which display prototrophic character for adenine are selected. The transformants are cultured in SW5 galactose-containing synthetic medium until a density of $2.2 \times 10^7$ cells per ml is reached, and the microsomal fractions are then prepared (Cullin, 1988; Renaud, 1990; Urban, 1990; Gautier, 1991). The microsomal fractions are tested for 7-ethoxyresorufin O-deethylase (EROD), testosterone 6beta-hydroxylase and benzo(a)pyrene monooxygenase activities as described above.

The results call for the following comments:

the over production of P450 reductase, in PES1-3 for example, induces a significant increase (from 5- to 10-fold depending on the conditions) in the specific activity (in enzyme turnover number) of the cytochromes P450 of the 1A1 family tested. This increase factor reaches from 40- to 60-fold in the case of human P450 3A4. Nevertheless, this increase in specific activity is accompanied, in the case of P450 1A1, by the destruction of a significant fraction of the enzyme, probably by oxidative processes which induce the conversion of the active P450 form to the inactive P420 form.

Figure 12:
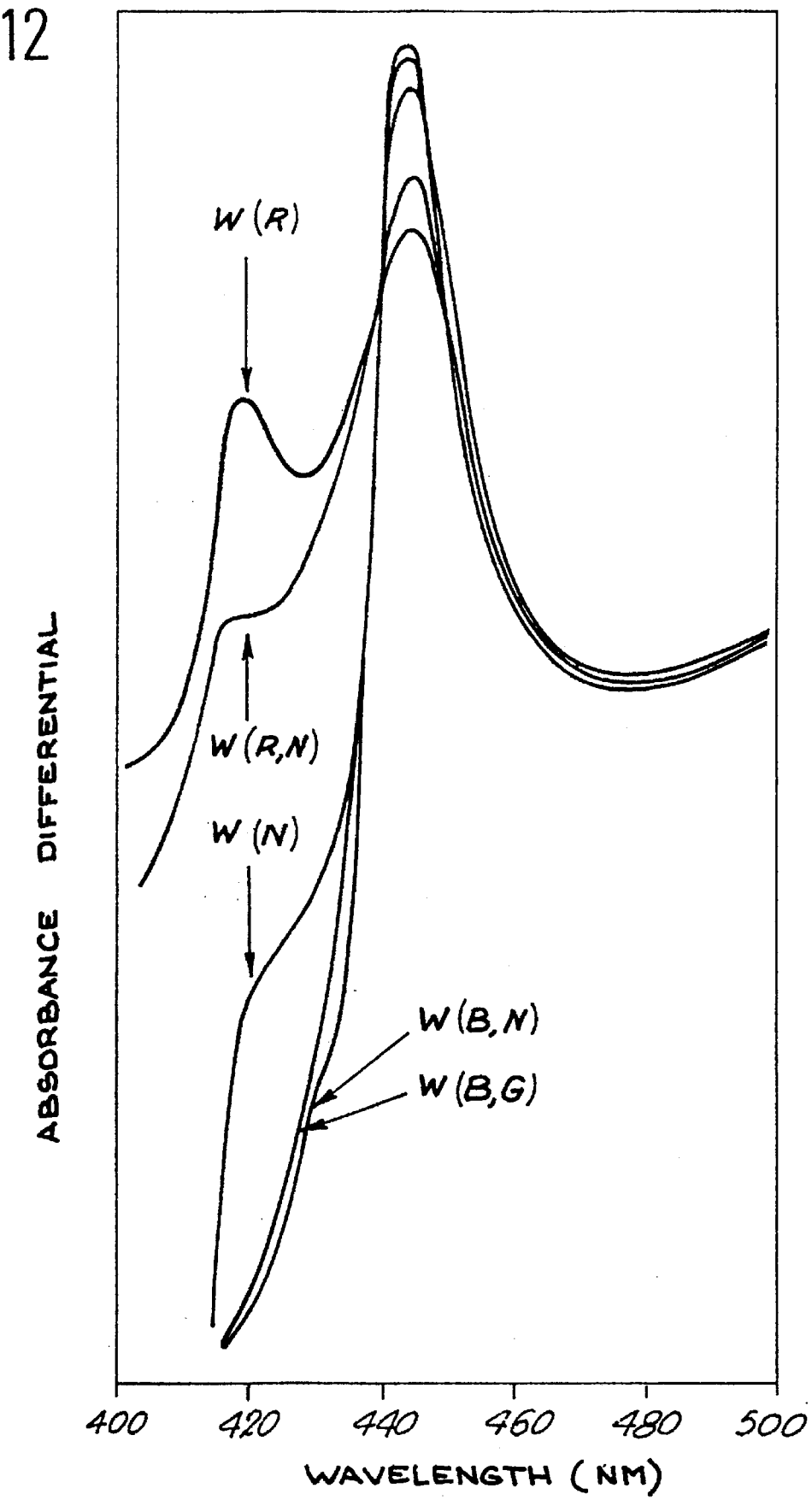
FIG. 12 illustrates a diagram showing the effects of the levels of expression of cytochrome b5 and reductases on the stability of human cytochrome P450 1A1.

FIG. 12 demonstrates this fact: in the strain PES1-2 (labeled W(N)), which expresses a wild-type level of reductase, only the presence of a slight shoulder in the spectrum of human P450 1A1 is detectable at 420 nm, indicating that the very large majority of P450 is in native form. In contrast, in the strain PES1-4 overexpressing the reductase (labeled W(R)), the spectrum of the P450 is strongly degraded and displays a maximum at 420 nm. In the strain PES1-34, which expresses human cytochrome b5 and which overexpresses the yeast reductase (labeled W(R,B)) the spectrum regains a normal appearance; in fact, the P420 denatured form becomes undetectable. Examination of Table 3 shows that the specific activity (in turnover number) of the P450 is also maximal under these conditions, despite the lower level of reductase present in the strain PES-1-34 compared to that in the strain EP1-3. This demonstrates that the expression of human cytochrome b5 in the strains overexpressing NADPH-cytochrome P450 reductase has the dual effect of stabilizing the P450 1A1 while permitting a maximal specific activity.

Nevertheless, the effect of the coexpression of human cytochrome b5 is variable, depending on the type of cytochrome P450 under consideration. In the case of cytochrome P450 3A4, no particular stabilization effect is observed. On the other hand, a strong activating effect is demonstrated. Table 3 shows that the expression of cytochrome b5 alone increases 7-fold the specific activity of P450 3A4 towards testosterone at a constant reductase level. When human cytochrome b5 is expressed at the same time as the reductase is overproduced, the gain in activity reaches the considerable value of 72-fold.

In conclusion, for both types of P450 tested, the production of human cytochrome b5 yields a considerable advantage, both in respect of stability and in respect of specific activity. A noteworthy point is that endogenous yeast cytochrome b5 appears to lack these specific effects despite its presence at a comparable, or even higher, level than that of human cytochrome b5 in some of the strains. Consequently, the nature (mammalian) of the cytochrome b5 proves to be an important factor.

Technical approaches enabling, in the strain PES1-34, the risks of genetic instability to be limited while permitting expression at a high level under the control of a single regulation of three heterologous genes, 1/ The use of the same inducible promoter for expression of the reductase, of cytochrome b5 and of P450, thereby enabling the toxic effects which might be linked to a permanent overproduction of these enzymes or to the resulting heterologous monooxygenase activity to be avoided.

2/ The use of the same genomic locus for the expression of two different heterologous genes in the form of a heterozygous diploid. This enables the combination events capable of resulting in an impairment of regulation or of the functions expressed to be limited.

3/ The use of expression plasmids for P450 using the same promoter as the integrated reductase and b5 genes, but different 3'-flanking sequences in order to avoid the risks of instability which might result from homologous recombinations between plasmid and genome.

4.4.3 Expression of Human Epoxide Hydrolase in the Strains PES1-5 and PES1-53 and Bioconversion of Benzo (a)Pyrene The assay of styrene oxide hydrolase activity in the strains PES1-5 and PES1-53 demonstrates the formation from styrene oxide of approximately 1 to 2 nmol of 2-phenyl-2-hydroxyethanol per min and per mg of microsomal proteins. This activity is undetectable in the other strains of the PES1 series. The reductase activity of the strain PES1-53 is comparable to that of the strain PES1-34. The strain PES1-53 transformed with an expression plasmid which codes for cytochrome P450 1A1 is capable, on incubation with benzo (a)pyrene, of hydrolysing the benzo(a)pyrene 7,8-oxide formed in situ to benzo(a)pyrene-7,8-diol. These activities are demonstrated in FIG. 13, which shows an HPLC separation of the metabolites of benzo(a)pyrene formed on incubation of this pollutant with strains PES1-2, PES1-3 and PES1-53 transformed to express murine cytochrome P450 1A1. Clearly, only the strain PES1-53 permits the formation of benzo(a)pyrene-7,8-diol in large amounts. This molecule is an important intermediate in the degradation of the carcinogenic industrial pollutant, benzo(a)pyrene.

5. Fields of Application

The field of application includes, as a first priority, the expression in yeast of the activities of any members of the superfamily of cytochromes P450, and the applications capable of being made thereof. In fact, the whole of the system described may be extended a priori to any multigenic heterologous expression system (even other than that of P450) which enables a complex function, such as a multistep heterologous biosynthesis, to be carried out.

bioconversions of any type (followed or otherwise by extraction of the products formed) depending on the isoenzymes of cytochromes P450 introduced, where appropriate multistep bioconversions by using the extensions mentioned.

The detection, identification, assay and destruction of miscellaneous toxic or carcinogenic pollutant substances (depending on the types of P450 introduced). This type of application may involve the coexpression of several cytochromes P450, of relay enzymes such as epoxide hydrolase, of deactivating enzymes such as glutathione transferases and glucoronate transferases and of transporters such as the "Multi-drugsresistance protein".

The production of in vitro systems for simulation of the metabolism of medicinal products in man, accurately reproducing human activities and including the possibility of analysing qualitatively and quantitatively the role of the different activities with respect to the nature and levels of the metabolites.

The following strains were deposited with the Collection Nationale de Cultures de Microorganismes [National Collection of Microorganism Cultures] of the Pasteur Institute, 25 rue du Docteur Roux, 75015 Paris, on Jul. 7, 1992:

PES 1-1 under No. 1-1230

PES 1-2 under No. 1-1231
PES 1-3 under No. 1-1232
PES 1-4 (S) * under No. 1-1233
*: S=sense
PES 1-4 (AS) ** (referred to as W(B)) under No. 1-1234
**: AS=antisense

TABLE 1

| Strain | Ploidie | Yred loc1 Locus 1 | Yred loc1 Locus 2 | URA3 | TRP1 |
|---|---|---|---|---|---|
| PES1-1 | hap (a) | WT | — | − | − |
| PES1-2 | hap (alpha) | WT | — | − | − |
| PES1-3 | hap (alpha) | Yred::GAL | — | + | − |
| PES1-3D | hap (a) | Del/TRP1 | — | − | − |
| PES1-3U | hap (alpha) | Yred::GAL | — | − | − |
| PES1-4 | hap (a) | DEL/b5::GAL | — | + | − |
| PES1-12 | dip | WT | WT | − | − |
| PES1-31 | dip | Yred::GAL | WT | + | − |
| PES1-34 | dip | Yred::GAL | Del/b5::GAL | + | − |
| PES1-42 | dip | WT | Del/b5::GAL | + | − |
| PES1-5 | hap (a1) | Del/HEH::GAL | — | + | − |
| PES1-53 | dip | Yred::GAL | Del/HEH::GAL | + | − |

Legend:
hap: haploid; dip: diploid
b5::GAL: human cytochrome b5 under the transcriptional control of GAL10-CYC1
HEH::GAL: human epoxide hydrolase under the transcriptional control of GAL10-CYC1
Del: deleted
WT: wild-type
Yred::GAL: Yred ORF under the transcriptional control of the GAL10-CYC1 promoter

TABLE 2

| Strain | Yred activity (a) (nmol/min/mg) L (d) | Yred activity (a) (nmol/min/mg) G (d) | Total cyt. b5 (b) (pmol/mg) L | Total cyt. b5 (b) (pmol/mg) G | Human cyt. b5 (c) (pmol/mg) L | Human cyt. b5 (c) (pmol/mg) G |
|---|---|---|---|---|---|---|
| PES1-1 | 53 | 53 | 73 | 60 | 0 | 0 |
| PES1-2 | 53 | 53 | 73 | 60 | 0 | 0 |
| PES1-12 | 53 | 53 | 73 | 60 | 0 | 0 |
| PES1-3* | 1738 | <1 | 73 | 102 | 0 | 0 |
| PES1-3D | 0 | 0 | ND | ND | 0 | 0 |
| PES1-4 | 0 | 0 | 162 | 88 | 82–160 | <1 |
| PES1-31 | 587 | 28 | ND | ND | 0 | 0 |
| PES1-34 | 560 | 27 | 99 | 85 | 40–80 | <1 |
| PES1-42 | 27 | 27 | 103 | 49 | 40–80 | <1 |

(a): measured as the NADPH-cytochrome reductase activity per mg of microsomal proteins
(b): (human cyt. b5 + endogenous yeast cyt. b5) determined by differential spectroscopy and calculated per mg of microsomal proteins
(c): estimated contribution of human b5 in the total b5
L: data obtained after culture in SWA5 medium
G: data obtained after culture in SWA6 medium
*: PES1-3 and PES1-34

TABLE 3

| Strain | P450 1A1 (Murine) (a) | P450 1A1 (Human) (b) | P450 3A4 (Human) (c) |
|---|---|---|---|
| PES1-2 | 1 | 1 | 1 |
| PES1-3 | 9.3 | 4.4 | 62 |
| PES1-4 | 0 | 0 | 0 |
| PES1-31 | — | 3.5 | 44 |
| PES1-34 | — | 5 | 73 |
| PES1-42 | — | 0.5 | 7 |
| PES1-53 | — | 3.5 | — |

Activities of cytochromes P450
(a), (b): activity tested as ethoxyresurufin O-deethylase, the absolute value for PES1-2 is (a): 1.5 nmol/nmol of P450/min; (b): 3.2 nmol P450/min;
(c): tested as testosterone 6 beta-hydroxylase activity, the absolute value for PES1-2 is 31 pmol/nmol of P450/min

We claim:

1. A diploid yeast strain having a chromosomal genome comprising
   at least one heterologous gene stably integrated at a heterozygous locus,
   an inducible and regulable promoter controlling the heterologous gene such that said heterologous gene is expressed when said promoter is active,
   a mating-type locus, and
   isogenic alleles at the remainder of loci of the chromosomal genome,
   wherein the heterozygous locus lacks a wild-type allele.

2. The yeast strain of claim 1, wherein the heterozygous locus comprises two alleles lacking sequence homology.

3. The yeast strain of claim 1, wherein homologous sequences of the heterozygous locus are oriented in opposite reading directions.

4. The yeast strain of claim 1 further comprising a selectable marker associated with one integrated heterologous gene.

5. The yeast strain of claim 1, wherein the heterozygous locus further comprises two different heterologous genes stably integrated at corresponding loci of different alleles of the chromosomal genome, forming a heterozygous diploid locus.

6. The yeast strain of claim 5, wherein the heterologous genes code for factors of a multistep bioconversion chain.

7. The yeast strain of claim 1 wherein the heterozygous locus further comprises an integrated gene selected from the group consisting of a yeast NADPH-cytochrome P450 reductase gene and a heterologous NADPH-cytochrome P450 reductase gene.

8. The yeast strain of claim 7, wherein the NADPH-cytochrome P450 reductase gene is stably integrated into an endogenous NADPH-cytochrome P450 reductase locus of the chromosomal genome.

9. The yeast strain of claim 7 further comprising an integrated heterologous cytochrome b5 gene at the heterozygous locus.

10. The yeast strain of claim 7 further comprising an integrated heterologous human epoxide hydrolase gene at the heterozygous locus.

11. The yeast strain of claim 1 further comprising an extrachromosomal cassette for expression of a heterologous gene.

12. The yeast strain of claim 11 wherein the heterologous gene of the extrachromosimaial cassette further comprises a cytochrome P450 gene.

13. The yeast strain of claim 1, wherein the strain belongs to the species *Saccharomyces cerevisiae*.

14. A method of expressing monooxygenase activity of a heterologous cytochrome P450 gene comprising:

integrating an NADPH-cytochrome P450 reductase gene and a cytochrome b5 gene into a locus of the chromosomal genome of a diploid yeast strain thereby forming a heterozygous diploid locus, said chromosomal genome including: a mating type locus; for each said gene, an inducible and regulable promoter controlling said gene; and isogenic alleles at the remainder of loci of the chromosomal genome, wherein the heterozygous diploid locus lacks a wild-type allele, transforming the diploid yeast strain with a plasmid carrying a cassette for expression of a heterologous cytochrome P450 gene, and expressing the monooxygenase activity of said heterologous cytochrome P450 gene.

15. The method of claim 14, wherein the cytochrome b5 gene of the integration step and the cytochrome P450 gene of the transformation step originate from a single heterologous species.

16. A set of yeast strains, each yeast strain having:

a chromosomal genome, an NADPH-cytochrome P450 reductase gene and a heterologous cytochrome b5 gene integrated into said chromosomal genome, the levels of expression of the NADPH-cytochrome P450 reductase and the cytochrome b5 genes being variable amongst the strains, and a plasmid carrying a cassette for the expression of a heterologous cytochrome P450 gene, said plasmid inserted into said chromosomal genome, wherein the strains of the set provide variable expression of the monooxygenase activity of the cytochrome P450 gene due to the variable levels of expression of the NADPH-cytochrome P450 reductase and the cytochrome b5 genes.

* * * * *